(12) United States Patent
Okamoto et al.

(10) Patent No.: US 7,745,616 B2
(45) Date of Patent: Jun. 29, 2010

(54) BEAD FOR ENANTIOMERIC ISOMER RESOLUTION AND PROCESS FOR PRODUCING THE SAME

(75) Inventors: Yoshio Okamoto, Aichi (JP); Chiyo Yamamoto, Aichi (JP); Tomoyuki Ikai, Aichi (JP); Masami Kamigaito, Aichi (JP)

(73) Assignees: National University Corporation, Nagoya University, Nagoya, Aichi (JP); Daicel Chemical Industries, Ltd., Osaka (JP)

(*) Notice: Subject to any disclaimer, the term of this patent is extended or adjusted under 35 U.S.C. 154(b) by 244 days.

(21) Appl. No.: 11/918,331

(22) PCT Filed: Apr. 28, 2006

(86) PCT No.: PCT/JP2006/309358

§ 371 (c)(1),
(2), (4) Date: Oct. 11, 2007

(87) PCT Pub. No.: WO2006/121060

PCT Pub. Date: Nov. 16, 2006

(65) Prior Publication Data

US 2009/0068468 A1    Mar. 12, 2009

(30) Foreign Application Priority Data

May 9, 2005    (JP)    ............................. 2005-135920

(51) Int. Cl.
*C08B 3/12* (2006.01)
(52) U.S. Cl. ...................... 536/123.1; 536/56; 436/529; 428/407
(58) Field of Classification Search ......... 428/402–407; 536/123.1, 56; 436/529
See application file for complete search history.

(56) References Cited

U.S. PATENT DOCUMENTS

| | | | | |
|---|---|---|---|---|
| 6,217,769 | B1 * | 4/2001 | Okamoto et al. | ............ 210/635 |
| 7,223,334 | B2 * | 5/2007 | Okamoto et al. | ......... 210/198.2 |
| 7,323,101 | B2 * | 1/2008 | Okamoto et al. | ......... 210/198.2 |
| 7,683,167 | B2 * | 3/2010 | Okamoto et al. | ............ 536/115 |
| 2006/0219615 | A1 | 10/2006 | Okamoto et al. | |

FOREIGN PATENT DOCUMENTS

| | | | |
|---|---|---|---|
| EP | A527235 A1 | * | 9/1992 |
| JP | 03-261729 | | 11/1991 |
| JP | 07-063622 | | 7/1995 |
| JP | 8-59702 | * | 3/1996 |
| WO | WO03/004534 | * | 1/2003 |
| WO | WO 2004/086029 | | 10/2004 |

* cited by examiner

*Primary Examiner*—Leszek Kiliman
(74) *Attorney, Agent, or Firm*—Flynn, Thiel, Boutell & Tanis, P.C.

(57) ABSTRACT

There is provided a process for producing beads for enantiomeric isomer resolution with a satisfactory separation efficiency. The beads for enantiomeric isomer resolution include a polysaccharide derivative, in which the polysaccharide derivative has a structure crosslinked at the 6-position hydroxy group of constituent units of the polysaccharide with a crosslinking agent. The process for producing the beads for enantiomeric isomer resolution includes: the step of adding dropwise an organic solvent solution of the polysaccharide derivative to a coagulation bath being stirred to thereby produce beads; the step of taking out the beads and then optionally drying the same after washing; and the step of reacting the beads with a crosslinking agent in an organic solvent to react at least part of the 6-position hydroxy groups in the constituent units of the polysaccharide with the crosslinking agent, thereby obtaining a reaction mixture containing beads having a crosslinked structure.

6 Claims, 3 Drawing Sheets

Fig. 2
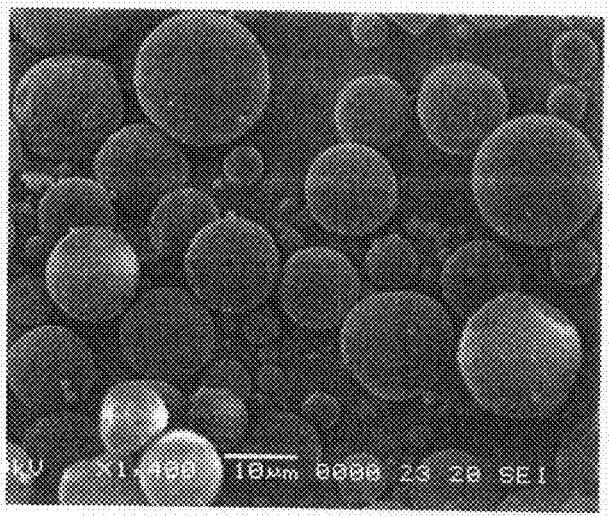
BEADS OF IK-10 AND IK-11
BEFORE CROSSLINKING
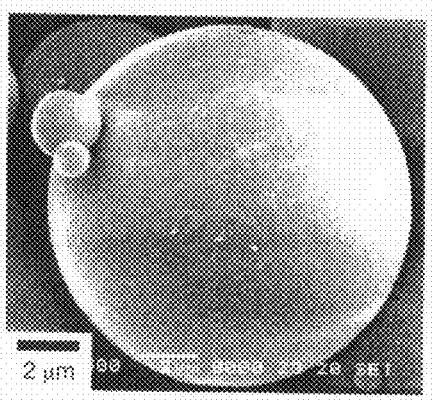
BEFORE DEPROTECTION AND
CROSSLINKING OF IK-14
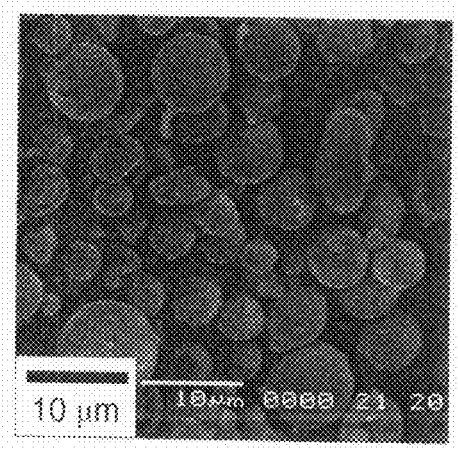
IK-14
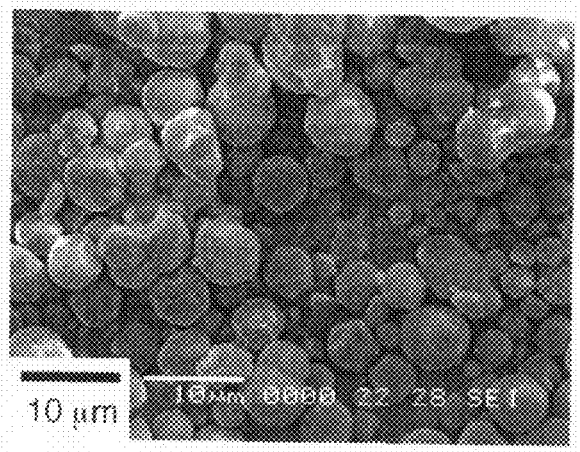
IK-17

BEAD FOR ENANTIOMERIC ISOMER RESOLUTION AND PROCESS FOR PRODUCING THE SAME

TECHNICAL FIELD

The present invention relates to beads for enantiomeric isomer resolution suitable as a filler for high performance liquid chromatography (HPLC), and a process for producing the same.

BACKGROUND ART

In recent years, the importance of an optically active compound has increased even more, and a process for selectively and efficiently producing a pure optically active chiral molecule from the viewpoint of research and development not only of pharmaceuticals but also of functional materials is indispensable.

The optical resolution by HPLC is developed as a process which can be used for both fractionation and microanalysis, and there has been progress in the development of various chiral fillers. Of those, a substance obtained by converting a polysaccharide which abundantly exists in nature, such as cellulose and amylose, to a phenylcarbamate derivative is widely used because such a substance has an excellent optical resolution ability to various kinds of racemates including pharmaceuticals, as a chiral stationary phase for HPLC.

In the chiral stationary phase using those polysaccharide derivatives, used as a filler is a derivative which is physically adsorbed on or chemically bonded to silica gel serving as a carrier. However, such a filler that is supported on silica gel in the above-mentioned manner cannot use, as an eluent, a solvent in which a polysaccharide derivative is swollen and/or dissolved. Further, the proportion of the polysaccharide derivative contained in the filler is small, and substantially, only the polysaccharide derivative on the surface of silica gel is used for optical resolution. Thus, in such a filler, there is room for improvement as a filler for fractionation.

JP-B-7-63622 discloses a separating agent formed of particles of 7 to 13 µm obtained by crushing and classifying polysaccharide derivatives in which 10% or more of hydroxyl groups were substituted with a carbamoyl group. Further, JP-B-7-63622 discloses, on page 2, column 4 that crosslinking may be performed as required, but there is no specific description.

DISCLOSURE OF THE INVENTION

The present invention provides beads of the non-crushed type for enantiomeric isomer resolution with a high optical resolution ability and an excellent separation efficiency, and a process for producing the same.

The present invention provides a bead for enantiomeric isomer resolution including a polysaccharide derivative, in which the polysaccharide derivative has a hydroxyl group at 6-position of constituent units of the polysaccharide and has a structure crosslinked at the hydroxyl group with a crosslinking agent.

The present invention provides a bead for enantiomeric isomer resolution including a polysaccharide derivative, in which the polysaccharide derivative has a structure crosslinked at a hydroxyl group that randomly remains at any of 2-, 3-, and 6-positions of constituent units of the polysaccharide with a crosslinking agent and the average number of remaining hydroxyl groups in all the constituent units of the polysaccharide derivative is one or less.

The present invention provides a process for producing beads for enantiomeric isomer resolution including a polysaccharide derivative, in which the polysaccharide derivative has hydroxyl groups at the 6-positions in the constituent units of the polysaccharide and has a structure crosslinked at the hydroxyl group with a crosslinking agent. The process for producing beads for enantiomeric isomer resolution includes the steps of: adding dropwise an organic solvent solution of the polysaccharide derivative to a coagulation bath while being stirred to thereby produce beads; taking out the beads, and then optionally drying the same after washing; and reacting the beads with a crosslinking agent in an organic solvent to react at least part of the 6-position hydroxyl groups in the constituent units of the polysaccharide with the crosslinking agent to thereby obtain a reaction mixture containing beads having a crosslinked structure.

The present invention provides a process for producing beads for enantiomeric isomer resolution including a polysaccharide derivative, in which the polysaccharide derivative has a structure crosslinked at hydroxyl groups that randomly remain at any of the 2, 3, and 6-positions in the constituent units of the polysaccharide with a crosslinking agent and the average number of remaining hydroxyl groups in all the constituent units of the polysaccharide derivative is one or less.

The process for producing beads for enantiomeric isomer resolution includes the steps of:

reacting a derivative-forming compound in an amount required for converting 66 to 95% of hydroxyl groups of all the hydroxyl groups of the polysaccharide to a carbamate group to thereby obtain a polysaccharide derivative;

adding dropwise an organic solvent solution of the polysaccharide derivative to a coagulation bath while being stirred to thereby produce beads;

taking out the beads and then optionally drying after washing; and reacting the beads with a crosslinking agent in an organic solvent to react at least part of the 6-position hydroxyl groups in the constituent units of the polysaccharide with a crosslinking agent to thereby obtain a reaction mixture containing beads having a crosslinked structure.

The beads for enantiomeric isomer resolution of the present invention are not supported on a conventional carrier, such as a silica gel, but have an optical-resolution ability equivalent to the conventional carrier supporting substances.

Further, the beads for enantiomeric isomer resolution of the present invention are applicable for a large-scale fractionation. This is because, in the case of columns having the same capacity, the beads for enantiomeric isomer resolution of the present invention make it possible to increase the amount of polysaccharide derivatives that can be packed in the column, as compared with a conventional carrier-supporting substance, whereby the separation efficiency (amount of racemates which can be resolved per unit quantity) can be improved. In particular, because the beads for enantiomeric isomer resolution of the present invention are spherical, the beads for enantiomeric isomer resolution of the present invention are more efficiently charged into a column, compared with non-spherical beads.

Further, the beads for enantiomeric isomer resolution of the present invention enable the use of a solvent for dissolving a polysaccharide derivative, which cannot be used in the conventional carrier-supporting substances, whereby an eluent can be selected from a wider selection range.

DETAILED DESCRIPTION OF THE INVENTION

<Beads for Enantiomeric Isomer Resolution>

The beads for enantiomeric isomer resolution of the present invention includes a polysaccharide derivative, in which the polysaccharide derivative has hydroxyl groups at the 6-positions in the constituent units of the polysaccharide and has a structure crosslinked at the hydroxyl group with a crosslinking agent.

The beads for enantiomeric isomer resolution of the present invention are not supported on a carrier, and are not crushed (particle sizes are not adjusted by crushing means).

The beads for enantiomeric isomer resolution of the present invention are globular or spherical, and the particle size is preferably within a range of 0.1 to 100 μm, more preferably 1 to 30 μm, and still more preferably 3 to 10 μm.

The beads for enantiomeric isomer resolution of the present invention may have a pore size which is similar to that of a porous material such as silica gel.

<Process for Producing Beads for Enantiomeric Isomer Resolution>

Hereinafter, the process for producing beads for enantiomeric isomer resolution of the present invention will be described. Specifically, the beads for enantiomeric isomer resolution of the present invention can be produced by any of processes described in Examples described later. Each of the following steps is neither independent nor separate, and one step may be divided into two or more steps, or two steps may be combined into one step. Alternatively, another step may be added suitably.

First, a polysaccharide derivative is produced in a first step. As a polysaccharide which leads a polysaccharide derivative to be produced in this process, any of synthetic polysaccharides, natural polysaccharides, and natural product-denatured polysaccharides may be used insofar as they are optically active. Preferable is a polysaccharide whose bonding manner is of high regularity.

Examples of the polysaccharide include: β-1,4-glucan (cellulose); α-1,4-glucan (amylose or amylopectin); α-1,6-glucan (dextran); β-1,6-glucan (pustulan); β-1,3-glucan (such as curdlan or schizophyllan); α-1,3-glucan; β-1,2-glucan (a Crown Gall polysaccharide); β-1,4-galactan; β-1,4-mannan; α-1,6-mannan; β-1,2-fructan (inulin); β-2,6-fructan (levan); β-1,4-xylan; β-1,3-xylan; β-1,4-chitosan; α-1,4-N-acetylchitosan (chitin); pullulan; agarose; and alginic acid. Starch containing amylose is also included.

Of those, cellulose, amylose, β-1,4-xylan, β-1,4-chitosan, chitin, β-1,4-mannan, inulin, curdlan, and the like are preferred because they easily enable highly pure polysaccharides to be obtained. Cellulose and amylose are particularly preferred.

The number average degree of polymerization of the polysaccharide (average number of pyranose or furanose rings in one molecule) is preferably 5 or more, or more preferably 10 or more, and has no particular upper limit. However, the number average degree of polymerization is preferably 1,000 or less in terms of the easiness of handling, and is more preferably 5 to 1,000, still more preferably 10 to 1,000, or particularly preferably 10 to 500.

The polysaccharide derivative capable of being used can be obtained by bonding a compound having a functional group capable of reacting with a hydroxyl group to some or all of the hydroxyl groups of the above-mentioned polysaccharide by, for example, ester bonding, urethane bonding, or ether bonding.

In the present invention, a process including the steps of: producing a polysaccharide derivative while protecting the hydroxyl groups at the 6-positions of polysaccharide by a protecting group; eliminating the protecting group by a deprotection reaction; and forming a hydroxyl group at part of or all of the 6-positions in all the constituent units may be applied to the manufacturing of a polysaccharide derivative. Of all the constituent units, the hydroxyl groups at the 6-positions remain by preferably 15% or more, and more preferably 30% or more.

In the present invention, a polysaccharide derivative can be produced by application of a process in which a predetermined amount of derivative-forming compound is reacted with a polysaccharide to thereby obtain a polysaccharide derivative. In the process, the used amount of the derivative-forming compound is an amount required for converting 66 to 95% of hydroxyl groups of all the hydroxyl groups of the polysaccharide into a carbamate group. In this reaction, a crosslinking agent is made to react with the hydroxyl groups which randomly remain at any of the 2-, 3-, and 6-positions in the constituent units of the polysaccharide, and it is not necessary to protect a specific hydroxyl group of the polysaccharide.

The polysaccharide derivative obtained by the process has a structure in which hydroxy groups randomly remain at any of the 2, 3, and 6-positions in the constituent units of the polysaccharide and the average number of remaining hydroxyl groups in all the constituent units of the polysaccharide derivative is one or less.

Examples of functional group-containing compounds that can react with a hydroxyl group include isocyanic acid derivatives, carboxylic acids, esters, acid halides, acid amide compounds, halides compounds, aldehydes, alcohols or other elimination group-containing compounds; and aliphatic, alicyclic, aromatic, and heteroaromatic compounds thereof.

Examples of a particularly preferable polysaccharide derivative include a polysaccharide ester derivative and a polysaccharide carbamate derivative.

In the next step, an organic solvent solution of the polysaccharide derivative obtained in the previous step is added dropwise to a coagulation bath, being stirred as required, to thereby produce beads.

As an organic solvent solution of a polysaccharide derivative, tetrahydrofuran (THF), acetone, ethyl acetate, chloroform, methylene chloride, N,N-dimethylacetamide, N,N-dimethylformamide (DMF), dimethyl sulfoxide (DMSO), pyridine, $C_{1-22}$ alcohols (preferably $C_{4-12}$ alcohols, and particularly preferably heptanol), and the like can be used alone or as a mixture of two or more of the above. A mixed solvent of an organic solvent (preferably THF) except alcohols and $C_{1-22}$ alcohols (preferably heptanol) are preferably used.

In the mixed solvent of an organic solvent except alcohols and $C_{1-22}$ alcohol, the content of alcohol is preferably 5 vol % or more, more preferably 10 vol % or more, still more preferably 10 to 40 vol %, and particularly preferably 25 to 35 vol %.

The concentration of a polysaccharide derivative in an organic solvent of a polysaccharide derivative is preferably 0.1 to 10 mass %, more preferably 0.3 to 5.0 mass %, and still more preferably 0.5 to 2.5 mass %.

Any coagulation bath can be used insofar as it can solidify the drops of the polysaccharide derivatives, and, for example, an aqueous surfactant solution can be mentioned, and particularly an aqueous anionic surfactant solution is preferable. As an anionic surfactant, fatty acid salt, rosin acid salt, alkyl sulfate, alkylbenzene sulfonate, alkyl diphenyl ether sulfonate, polyoxyethylene alkyl ether sulfate, sulfosuccinic acid diester, α-olefin sulfuric acid ester, α-olefin sulfonate, or the like can be used.

The temperature of the coagulation bath is preferably 50 to 100° C., more preferably 60 to 90° C., and still more preferably 75 to 80° C.

In order to form the beads to be obtained into a globular shape and desirably a sphere shape, a coagulation bath is stirred during or after the dropwise adding of the organic solvent solution of the polysaccharide derivative. When a six blade-type stirring device in a 1 L container is used, stirring is performed at preferably 100 to 3,000 r/m, more preferably 500 to 2,000 r/m, and still more preferably 800 to 1,200 r/m.

Beads with pores can be produced by a process including: dissolving a polysaccharide derivative and an additive for forming pores in an organic solvent; preparing beads in the same manner as described above; and washing the prepared beads with a solvent for dissolving only the additive for forming pores contained in the beads. As the additive for forming pores, polymers such as poly(N-isopropylacrylamide) (PNIPAM), and polymethylmethacrylate (PMMA) can be used.

In the following step, the beads prepared in the previous step are taken out, and, as required, dried after being washed. The organic solvent used in the previous step is preferably removed by distilling off or the like prior to this step.

The beads can be washed with methanol or the like after taking-out by a known filtration process such as suction filtration. Then, the beads are dried by a known drying method such as vacuum drying. After drying, in order to make the particle sizes uniform, beads with excessively large particle diameters and beads with excessively small particle diameters may be removed using a filter or the like, if necessary.

In the following step, the beads obtained in the previous step are made to react with a crosslinking agent in an organic solvent, to react at least part of the 6-position hydroxyl groups in the constituent units with a crosslinking agent, thereby obtaining a reaction liquid containing beads of a crosslinking structure.

As a crosslinking agent, isocyanate compounds having two or more isocyanate groups in a molecule, such as 4,4-diphenylmethane diisocyanate, tolylene diisocyanate, hexamethylene diisocyanate, dicarboxylic acid and halides thereof, amides, and esters can be used.

The reaction between the polysaccharide derivative and the crosslinking agent is performed in the presence of an organic solvent such as acetone, toluene, benzene, pyridine, dimethyl sulfoxide, chloroform, methylene chloride, ethyl acetate, DMA, DMF.

The reaction temperature is 80 to 90° C. and the reaction time is 24 to 36 hours. When a product generated in the middle of the reaction is sampled and dissolved in THF, if the sample product is not dissolved, the crosslinking reaction can be considered to be completed.

After the completion of the crosslinking reaction, the beads are collected by suction filtration or the like, washed with warmed methanol or the like to remove unnecessary substances, and then dried under vacuum or the like.

The beads for enantiomeric isomer resolution of the present invention can be used for separating the enantiomeric isomer from a racemate, as a filler for HPLC. In addition, the beads for enantiomeric isomer resolution of the present invention are also applicable to supercritical fluid chromatography, column chromatography, thin layer chromatography, gas chromatography, capillary chromatography, and the like.

BRIEF DESCRIPTION OF THE DRAWINGS

FIG. 2 shows SEM photographs of the beads in each phase of each Example.

EXAMPLES

Figure 1:
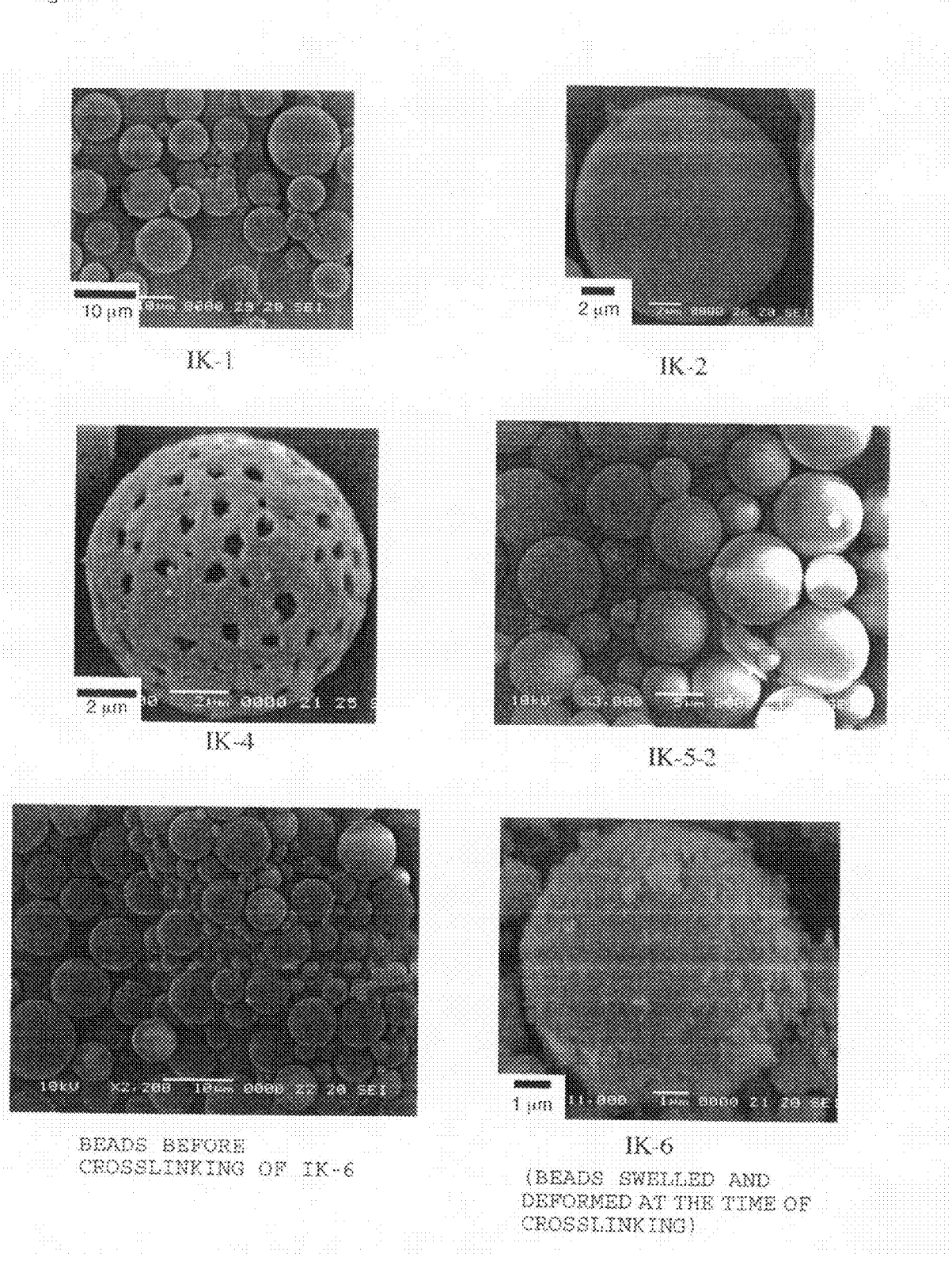
FIG. 1 shows SEM photographs of the beads in each phase of each Example.

Embodiments of the present invention will be described by way of the following examples. The examples are given solely for the purpose of illustration of the present invention and are not to be construed as limitations of the present invention.

The details of the reagents used in the following examples are as follows.

(1) Reagents
Cellulose (Avicel): degree of polymerization of 200, manufactured by Merck Ltd.
Amylose: degree of polymerization of 300, manufactured by Ajinoki Co., Ltd.
Cellulose beads: Celluflow C-25 manufactured by Chisso Corporation
Silica gel: Daiso gel SP-1000 (particle size: 7 μm, pore size: 100 nm) that has undergone amino propylation for surface treatment
Triphenylmethyl chloride (TrC1): manufactured by Kishida Chemical Co., Ltd.
3,5-dimethylphenylisocyanate: manufactured by Sigma-Aldrich Corp.
4,4'-diphenylmethane diisocyanate: manufactured by Tokyo Chemical Industry Co., Ltd.
4,4'-dibenzyl diisocyanate: synthesized by reacting 4,4'-ethylenedianiline with triphosgene
4,4'-ethylenedianiline: manufactured by Tokyo Chemical Industry Co., Ltd.
Triphosgene: manufactured by Tokyo Chemical Industry Co., Ltd.
Hexamethylene diisocyanate: manufactured by Tokyo Chemical Industry Co., Ltd.
m-xylylene diisocyanate: manufactured by Tokyo Chemical Industry Co., Ltd.
Tolylene-2,4-diisocyanate: manufactured by Tokyo Chemical Industry Co., Ltd.
Lithium chloride (Licl): manufactured by Wako Pure Chemical Industries, Ltd.
N,N-dimethylacetamide (DMA) (dehydrated): manufactured by Kanto Chemical Co., Inc.
Pyridine (dehydrated): Kanto Chemical Co., Inc.
Toluene (dehydrated): manufactured by Kanto Chemical Co., Inc.
Heptanol: manufactured by Kishida Chemical Co., Ltd. or manufactured by Wako Pure Chemical Industries, Ltd.
Racemates: synthesized product of commercial available product (2) Devices
Stirring device used for producing beads: SMT Multidisperser PB95
Shaft: PH-4 (6 blades)

(3) Measuring devices
NMR: Varian Gemini-2000 ($^1$H-400 MHz)
IR: JASCO FT/IR-620

HPLC: JASCO PU-980, UV-970, OR-990, MD-2010
SEM: JEOL JSM-5600
BET: hand-made by Satsuma Laboratory of Chemical and Biological Engineering Department, Graduate School of Engineering in Nagoya University Example 1

(1) Synthesis of Cellulose 3,5-dimethylphenyl carbamate OD(6-OH)-20 having Hydroxyl Groups in Part at the 6-positions According to the following reaction formula, cellulose 3,5-dimethylphenyl carbamate was synthesized.

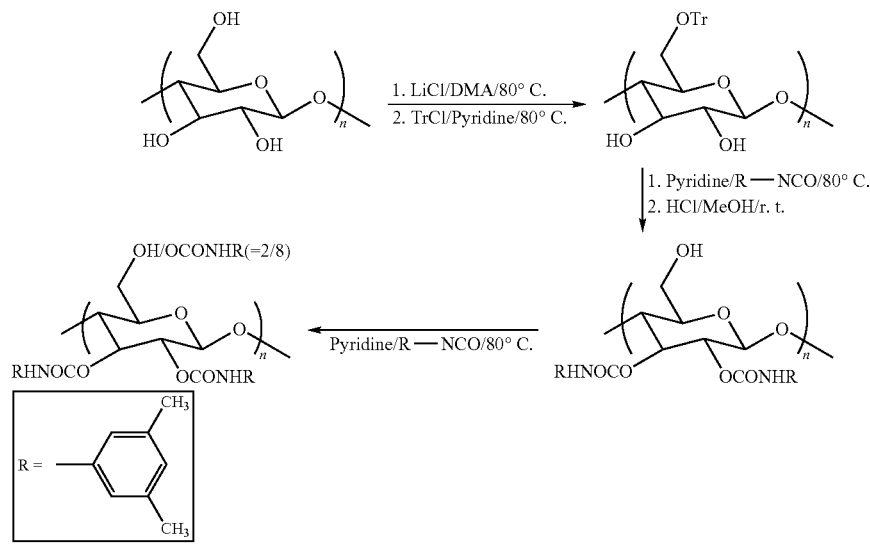

15 g of lithium chloride and 150 ml of dehydrated N,N dimethylacetamide were added to 10 g (62 mmol) of dried cellulose, and the mixture was swelled at 80° C. for 27 hours under a nitrogen atmosphere. Then, 32 g (114 mmol) of triphenyl methyl chloride and 150 ml of pyridine were added to the resultant for reaction at 80° C. for 24 hours. A pyridine soluble part was dropped into methanol to collected as an insoluble part. Then, the insoluble part was dried under vacuum.

Because the hydroxyl groups at the 6-positions of the glucose rings of the obtained derivatives were not completely tritylated, 15 g of lithium chloride and 150 ml of dehydrated N,N dimethylacetamide were again added to the derivative. The resultant mixture was swelled at 80° C. for 24 hours under a nitrogen atmosphere. Then, 17 g (62 mmol) of triphenyl methyl chloride and 150 ml of pyridine were added to the resultant for reaction at 80° C. for 24 hours. A pyridine soluble part was dropped into methanol to collect an insoluble part. Then, the insoluble part was dried under vacuum, yielding a derivative in which the hydroxyl groups at the 6-positions of the glucose rings were tritylated.

Next, 21 g of the obtained derivative was dissolved in 190 ml of pyridine, and 22 g (150 mmol) of 3,5-dimethylphenyl isocyanate was added under a nitrogen atmosphere for reaction at 80° C. for 30 hours. The reaction solution was sampled for measurement of infrared absorption spectrometry to confirm the presence of unreacted isocyanate in the solution. Then, the reaction solution was dropped into methanol to collect as an insoluble substance, yielding cellulose 2,3-bis (3,5-dimethylphenylcarbamoyl)-6-0-tritylcellulose.

Next, this derivative was stirred in 1,500 ml of 1% HCl/methanol for 24 hours for deprotection, thereby returning the groups at the 6th positions to hydroxyl groups. The resultant was washed with methanol and dried under vacuum, yielding 24 g of target cellulose 2,3-bis(3,5-dimethylphenyl carbamate).

Next, 10 g (22 mmol) of the obtained derivative was dissolved in 65 ml of pyridine, and 2.5 g (17 mmol) of 3,5-dimethylphenyl isocyanate was added under a nitrogen atmosphere for reaction at 80° C. for 18 hours. The reaction solution was dropped into methanol to collect an insoluble substance. The insoluble substance was dried under vacuum, yielding 9.5 g of cellulose 3,5-dimethylphenyl carbamate with a hydroxyl group in part at the 6-positions. The NMR analysis showed that about 20% of the hydroxyl groups at the 6-positions of the glucose rings remained. Hereinafter, this derivative is referred to as OD(6-OH)-20.

(2) Preparation of Cellulose Derivative Beads (OD(6-OH)-20 Beads)

First, 0.25 g of OD(6-OH)$_{20}$ was dissolved in 30 ml of a mixed solvent of tetrahydrofuran/heptanol (2/1, v/v). The resultant mixture was dropped in 500 ml of a 0.2% aqueous sodium lauryl sulfate solution heated to 75° C. in a water bath while being stirred with a disperser at a shaft rotation number of 1,100 rpm. Also after the completion of the dropping, a surfactant solution was heated to 75° C. for distilling tetrahydrofuran off.

The formed beads were collected through suction filtration and washed with methanol. After washing, the beads were dried under vacuum, yielding 0.22 g of OD(6-OH)-20 beads. In the process, the yield of the beads was about 87%. This operation was repeated, and the obtained beads were classified with a 20-μm filter, to thereby collect beads whose particle sizes range from about 3 to 10 μm. A six blade-type shaft was used for the disperser, and a 1-L beaker was used as the vessel. The obtained beads were subjected to observation with a scanning electron microscope (SEM).

(3) Crosslinking of Cellulose Derivative Beads Using Diisocyanate

In order to provide strength to the obtained polysaccharide derivative beads, hydroxyl groups at 6-positions and diisocyanate were reacted for crosslinking in the beads.

20 ml of toluene was added to 1.83 g of dried OD (6-OH)-20 beads under a nitrogen atmosphere, and the mixture was heated at 80° C. for 4 hours to swell the beads. Then, 0.3 g (1.2 mmol, excess amount) of 4,41-diphenylmethane diisocyanate was added thereto for reaction at 80° C. for 24 hours. The presence of unreacted isocyanate was confirmed by Liquid IR measurement of a supernatant, and a small amount of beads was sampled to confirm that the beads became insoluble in tetrahydrofuran. Then, the beads were collected through suction filtration, and were washed with warmed methanol while being suctioned, to thereby remove urea generated from excess isocyanate.

The absence of urea was confirmed by Solid IR measurement of the beads, and then the beads were dried under vacuum, to thereby obtain 1.83 g of beads in which about 20% of hydroxyl groups at the 6-positions were crosslinked to one another (hereinafter, referred to as crosslinked beads A, particle size of 5 to 7 μm).

(4) Packing of Beads into Columns for HPLC

The obtained crosslinked beads A were classified according to the particle size and were dispersed in 30 ml of hexane/paraffin liquid (2/1). The beads were packed into a stainless steel column with a length of 25 cm and an inner diameter of 0.2 cm under a pressure of 30 kg/cm² by using hexane/2-propanol (9/1) through a slurry process (Column IK-1, FIG. 1). For comparison, the conventional silica gel-carried type column was produced as follows. Fillers in which 21 wt % of cellulose tris (3,5-dimethylphenylcarbamate) was supported on an aminopropylized silica gel (particle size of 7 μm, pore size of 100 nm) were packed in a column according to the above-mentioned procedure. During the packing process, the pressure was first adjusted to 400 kg/cm² for several minutes, and then adjusted to 100 kg/cm².

(5) Optical Resolution of a Racemate by HPLC

Optical resolution of the following 10 kinds of racemates (3 to 12) was performed using the crosslinked-beads column obtained by the above-mentioned operation.

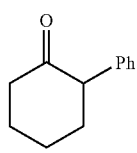
3

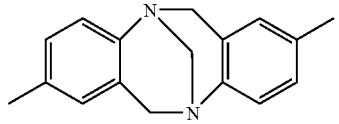
4

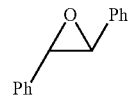
5

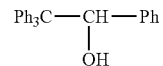
6

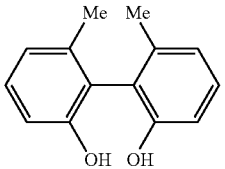
7

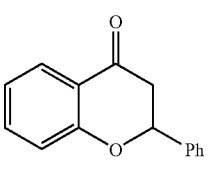
8

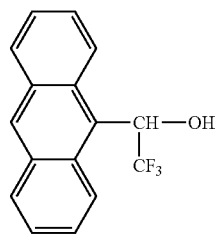
9

Co(acac)₃   10

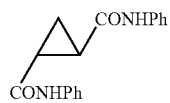
11

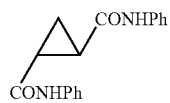
12

Hexane/2-propanol (90/10) and hexane/chloroform/2-propanol (90/10/1) were used as eluents, and a flow rate was 0.1 ml/min. A theoretical plate number N was determined from a chart of benzene, and a time $t_0$ at which a substance not retained by the column passes through the column was determined from an elution time of 1,3,5-tri-tert-butylbenzene. The evaluation results of the optical resolution ability of Column IK-1 are shown in Table 1. For comparison, the results of OD coated-type (silica gel-carried type) are also shown.

TABLE 1

| Compound | IK-1[a] H/I = 90/10 $k_1'$ | α | IK-1[a] H/C/I = 90//10/1 $k_1'$ | α | OD coated-type[a] H/I = 90/10 $k_1'$ | α |
|---|---|---|---|---|---|---|
| 2-phenylcyclohexanone | 3.75 (−) | 1.19 | 4.52 (−) | 1.25 | 0.84 (−) | 1.11 |
| Troger's base | 3.45 (+) | 1.20 | 4.23 (+) | 1.25 | 0.79 (+) | 1.21 |
| trans-stilbene oxide (Ph-epoxide-Ph) | 2.35 (−) | 1.67 | 3.00 (−) | 2.03 | 0.54 (−) | 2.33 |
| Ph$_3$C—CH(OH)—Ph | 4.91 (+) | 1.18 | 8.82 (+) | ~1[b] | 1.02 (+) | 1.33 |
| 6,6'-dimethyl-2,2'-biphenyldiol | 5.34 (−) | 2.77 | — | — | 2.04 (−) | 1.70 |
| Ph—CH(OH)—C(O)—Ph (benzoin) | 8.18 (+) | 1.33 | 12.1 (+) | 1.42[b] | 2.71 (+) | 1.64 |
| 2-phenyl-4-chromanone | 4.79 (−) | 1.21 | 5.60 (−) | 1.21 | 1.03 (−) | 1.45 |
| Co(acac)$_3$ | 1.71 (+) | 1.33 | 1.12 (+) | ~1 | 0.29 (+) | ~1 |
| 9-anthryl-CH(OH)-CF$_3$ | 8.84 (−) | 2.77 | 63.6 (−) | 3.46[b] | 1.43 (−) | 3.28 |
| trans-1,2-bis(N-phenylcarbamoyl)cyclopropane | 3.73 (+) | 1.40 | — | — | 0.52 (+) | 3.21 |

[a] Column: 25 × 0.20 cm(i.d.), flow rate: 0.1 ml/min.
[b] Column: 25 × 0.20 cm(i.d.), flow rate: 0.15 ml/min.

Comparison between the beads column and the conventional silica gel-carried type column in the α values with respect to various racemates showed that the optical resolution ability of the beads column is almost equivalent to that of the conventional silica gel-carried type column, although there are slight variations. The variations are presumably because the higher order structure of the derivative, which had been crosslinked, for use in the beads column was slightly different from that of the derivative which had been completely derivatized.

The durability against a solvent was improved by performing crosslinking in the beads. Chloroform, which was not used conventionally, could be contained in an eluent. Thus, the optical resolution ability was evaluated using an eluent containing chloroform. Note that substances in which a racemate strongly interacted with a filler and elution was not possible were not able to be analyzed, and thus the results of the substances are not shown.

Using an eluent of H/C/I (90/10/1), the optical resolution ability was overall improved. By changing an eluent as described above, there are advantages that the optical resolution results are improved and the solubility of an eluent of a sample is improved at the time of fractionation. Thus, it is extremely useful that an eluent can be appropriately selected from various solvents.

Example 2

(1) Synthesis of Cellulose 3,5-dimethylphenyl carbamate OD(6-OH)-70 having Hydroxyl Groups in Part at the 6-positions 45 ml of dehydrated N,N-dimethylacetamide was added to 1.5 g (9.3 mmol) of dried cellulose, and the mixture was swelled at 80° C. for 10 hours under a nitrogen atmosphere. The resultant was allowed to cool to room temperature. Then, 3.0 g of lithium chloride was added thereto, and the mixture was stirred for 3 hours at room temperature to thereby uniformly dissolve the cellulose.

Then, 20 ml of pyridine and 1.9 g (6.9 mmol) of triphenylmethyl chloride were added thereto for reaction at 80° C. for 40 hours. Then, 6.0 g (41 mmol) of 3,5-dimethylphenyl isocyanate was added for further reaction at 80° C. for 24 hours.

The reaction solution was sampled for measurement of infrared absorption spectrometry to confirm the presence of unreacted isocyanate in the solution. Then, the reaction solution was dropped into methanol to collect an insoluble substance, yielding cellulose 2,3-bis(3,5-dimethylphenyl-carbamoyl) -6-0-tritylcellulose.

Then, the derivative was stirred in 300 ml of 1% HCl/methanol for 40 hours for deprotection, to thereby return the groups at the 6-positions into hydroxyl groups. Then, the resultant was washed with methanol and dried under vacuum, to thereby obtain 4.3 g of target cellulose 2,3-bis(3,5-dimethylphenylcarbamate). The NMR analysis showed that about 70% of the hydroxyl groups at the 6-positions of the glucose rings remained. Hereinafter, this derivative is referred to as OD(6-OH)-70.

(2) Preparation of Cellulose Derivative Beads (OD(6-OH)-70 Beads)

0.75 g of OD(6-OH)-70 was dissolved in 30 ml of a mixed solvent of tetrahydrofuran/heptanol (2/1, v/v). The resultant mixture was dropped in 500 ml of a 0.2% aqueous sodium lauryl sulfate solution heated to 75° C. in a water bath while being stirred with a disperser at a shaft rotation number of 1,100 rpm. Also after the completion of the dropping, a surfactant solution was heated to 75° C. for distilling tetrahydrofuran off.

The formed beads were collected through suction filtration and washed with methanol. After washing, the beads classified with a 20-μm filter were dried under vacuum, yielding 0.58 g of OD(6-OH)-70 beads whose particle sizes range from about 3 to 10 μm. In the process, the yield of the beads was about 77%. This operation was repeated to thereby obtain 3.3 g of OD(6-OH)-70 beads. A six blade-type shaft was used for the disperser, and a 1-L beaker was used as the vessel.

(3) Treatment after Crosslinking (Tert-butyl Alcohol and Methanol)

10 ml of toluene was added to 1.0 g of dried OD(6-OH)-70 beads under a nitrogen atmosphere, and the mixture was heated at 80° C. for 4 hours to swell the beads. Then, 58 mg (0.23 mmol, excess amount) of 4,4-diphenylmethane diisocyanate was added thereto for reaction at 80° C. for 18 hours.

Then, 290 mg (2.0 mmol) of 3,5-dimethylphenyl isocyanate was added thereto for reaction at 85° C. for 22 hours. The presence of unreacted isocyanate was confirmed by Liquid IR measurement of a supernatant, and a small amount of beads was sampled to confirm that the beads became insoluble in tetrahydrofuran. About half of the reaction solution was dropped into methanol to crush residual isocyanate.

The beads were collected by suction filtration of the methanol solution. Then, the beads were thoroughly washed with warmed methanol while being suctioned, to thereby remove urea generated from isocyanate and methanol. The absence of urea was confirmed by Solid IR measurement, and then the beads were dried under vacuum, to thereby obtain 0.46 g of beads treated with methanol. A beads column which was packed with the obtained beads in the same procedure as in 3-1-4 is referred to as Column IK-10.

10 ml of tert-butanol (excess amount) was added to the other half of the reaction solution for reaction for 3 hours. The disappearance of isocyanate was confirmed by Liquid IR measurement of a supernatant, and the beads were collected through suction filtration. Then, the beads were washed with warmed methanol while being suctioned, to thereby remove urea generated from isocyanate and tert-butanol. The absence of urea was confirmed by Solid IR measurement, and 1.0 g of beads treated with tert-butanol was obtained. A beads column which was packed with the obtained beads in the same process as in the item (4) of Example 1 is referred to as Column IK-11.

(4) Optical Resolution of a Racemate by HPLC

Optical resolution of the 10 kinds of racemates (3 to 12) of Example 1 was performed using the crosslinked-beads column obtained by the above-mentioned operation. Hexane/2-propanol (90/10) was used as an eluent, and a flow rate was 0.1 ml/min. A theoretical plate number N was determined from a chart of benzene, and a time $t_0$ at which a substance not retained by the column passes through the column was determined from an elution time of 1,3,5-tri-tert-butylbenzene. The evaluation results of the optical resolution ability of Column IK-10 and Column IK-11 are shown in Table 2. For comparison, the results of OD coated-type (silica gel-carried type) are also shown.

TABLE 2

| racemates | IK-10 H/I = 90/10 | | IK-11 H/I = 90/10 | | OD coated-type H/I = 90/10 | |
|---|---|---|---|---|---|---|
| | $k_1'$ | α | $k_1'$ | α | $k_1'$ | α |
| 2-phenylcyclohexanone | 4.69 (−) | 1.21 | 4.63 (−) | 1.16 | 0.84 (−) | 1.11 |
| Tröger's base | 3.86 (+) | 1.32 | 3.27 (+) | 1.25 | 0.79 (+) | 1.21 |
| trans-stilbene oxide | 2.97 (−) | 1.60 | 2.51 (−) | 1.70 | 0.54 (−) | 2.33 |
| Ph₃C—CH(OH)—Ph | 6.58 (+) | 1.07 | 5.21 (+) | 1.09 | 1.02 (+) | 1.33 |
| 3,3'-dimethyl-2,2'-dihydroxybiphenyl | 6.84 (−) | 2.21 | 5.44 (−) | 2.27 | 2.04 (−) | 1.70 |
| Ph—CH(OH)—C(O)—Ph | 9.80 (+) | 1.33 | 7.89 (+) | 1.36 | 2.71 (+) | 1.64 |
| 2-phenylchroman-4-one | 5.73 (−) | 1.21 | 4.63 (−) | 1.24 | 1.03 (−) | 1.45 |
| Co(acac)₃ | 2.19 (+) | 1.23 | 1.84 (+) | 1.20 | 0.29 (+) | ~1 |
| 9-anthryl-CH(OH)-CF₃ | 9.90 (−) | 2.31 | 7.83 (−) | 2.41 | 1.43 (−) | 3.28 |
| trans-1,2-bis(N-phenylcarbamoyl)cyclopropane | 5.24 (+) | 1.41 | 3.84 (+) | 1.53 | 0.52 (+) | 3.21 |

Column: 25 × 0.20 cm(i.d.), flow rate: 0.1 ml/min

Table 2 shows that the optical resolution ability of IK-11 is overall higher than that of IK-10, and that a higher optical resolution ability can be achieved by treatment with tert-butyl alcohol. It is considered that, in Column IK-10, the optical resolution ability was decreased because part generated by reaction between isocyanate of one crosslinking agent and methanol interacted with a racemate not in an enantioselective way. In contrast, in Column IK-11, it is considered that the α values were increased due to the fact that, by treatment with a bulky tert-butyl alcohol, a non-selective interaction between a racemate and the unreacted part of the crosslinking agent did not occur, and interaction occurred only at an asymmetric discrimination site.

Unlike the preparation of the crosslinked beads for Column IK-10, a substance, in which only one of the two isocyanates of 4,4'-diphenylmethane diisocyanate was reacted with a derivative, was treated with a bulky tert-butyl alcohol in Column IK-11. Thus, it is expected that the interaction which participates in the optical resolution of the beads and a racemate works more effectively without interference by excessive interaction.

Example 3

(1) Synthesis of 4,4'-dibenzyl diisocyanate (Crosslinking Agent)

To a 500 ml three-neck flask, 10 g of 4,4'-ethylenedianiline and 200 ml of toluene were added. Hydrochloric acid gas generated from NaCl and sulfuric acid was blown into the mixture to convert the 4,4'-ethylenedianiline into hydrochloride. Then, a solution of 11 g of triphosgene dissolved in 100 ml of toluene was gradually added to the flask heated to 80° C. using a dropping funnel. 4 hours later, a substance in which 7 g of triphosgene was dissolved in 50 ml of toluene was further added gradually using a dropping funnel, and the heating was stopped 16 hours later.

The reaction system was not uniform and was divided into a toluene soluble part and a toluene insoluble part. Thus, only the toluene soluble part was moved to a 300-ml eggplant flask, and suction was performed with a vacuum pump to remove the toluene, yielding a pale yellow solid isocyanate. By IR and NMR, it was confirmed that a target 4,4'-dibenzyl diisocyanate was generated. The obtained isocyanate had high boiling point and could not be distilled, and thus production was not observed (yield amount: 6 g, yield: 50%).

(2) Synthesis of Cellulose 3,5-dimethylphenyl carbamate OD(6-Tr) having Trityl Groups at the 6-positions 300 ml of dehydrated N,N-dimethylacetamide was added to 10 g (62 mmol) of dried cellulose, and the mixture was swelled at 80° C. for 20 hours under a nitrogen atmosphere. The resultant was cooled to room temperature. Then, 4 g of LiCl was added thereto, and the mixture was stirred for 3 hours at room temperature to thereby dissolve cellulose. After the dissolving, 150 ml of pyridine and 23 g (83 mmol) of triphenylmethyl chloride were added thereto for reaction at 105° C. for 36 hours. Further, 26 g (177 mmol) of 3,5-dimethylphenyl isocyanate was added for further reaction at 80° C. for 24 hours.

The reaction solution was sampled for measurement of infrared absorption spectrometry to confirm the presence of unreacted isocyanate in the solution. Then, the reaction solution was dropped into methanol to collect an insoluble substance, yielding 36 g of cellulose 2,3-bis(3,5-dimethylphenylcarbamoyl) -6-0-trityl cellulose OD(6-Tr).

(3) Preparation of OD(6-Tr) Beads (3-3-3.)

First, 0.75 g of OD(6-Tr) was dissolved in 30 ml of a mixed solvent of tetrahydrofuran/heptanol (2/1, v/v). The resultant mixture was dropped in 500 ml of a 0.2% aqueous sodium lauryl sulfate solution heated to 75° C. in a water bath while being stirred with a disperser at a shaft rotation number of 1,100 rpm. Also after the completion of the dropping, a surfactant solution was heated to 75° C. for distilling tetrahydrofuran off.

The formed beads were collected through suction filtration and washed with methanol. After washing, the beads were dried under vacuum, yielding 0.42 g of OD(6-Tr) beads. In the process, the yield of the beads was about 56%. This operation was repeated, and the obtained beads were classified with a 20-μm filter, to thereby collect beads whose particle sizes range from about 3 to 10 μm. A six blade-type shaft was used for the disperser, and a 1-L beaker was used as the vessel. The obtained beads were subjected to observation with a SEM.

(4) Preparation of OD(6-OH)-100 Beads 2.5 g of OD(6-Tr) beads prepared in the above item (3) was stirred in 300 ml of 1% HCl/methanol at room temperature for 36 hours for deprotection, thereby returning the groups at the 6-positions to hydroxyl groups. The resultant was washed with methanol and dried under vacuum, yielding 1.7 g of target OD(6-OH)-100 beads. NMR and elementary analysis confirmed that 99% or more of the trityl groups introduced into the 6-positions were removed.

(5) Preparation of Crosslinked Beads using 4,4'-DBDI (for Column IK-14)

7 ml of toluene was added to 610 mg (1.48 mmol) of dried OD(6-OH)-100 beads under a nitrogen atmosphere, and the mixture was heated at 80° C. for 3 hours to swell the beads. Then, 90 mg (0.34 mmol) of 4,4'-dibenzyldiisocyanate (4,4'-DBDI) was added thereto for reaction at 80° C. for 33 hours.

The presence of unreacted isocyanate was confirmed by Liquid IR measurement of a supernatant, and a small amount of beads was sampled to confirm that the beads became insoluble in tetrahydrofuran. After that, 646 mg (4.39 mmol) of 3,5-dimethylphenyl isocyanate was added for reaction for 24 hours. Then, 5 ml (excess amount) of tert-butanol was added for reaction at 80° C. for 6 hours, to thereby process, with a bulky alcohol, a substance in which only one of the two isocyanates of 4,4'-DBDI was reacted with a derivative.

The disappearance of isocyanate was confirmed by Liquid IR measurement of a supernatant, and the beads were collected through suction filtration. Then, the beads were washed with warmed methanol while being suctioned, to thereby remove urea generated from isocyanate and tert-butanol.

The absence of urea was confirmed by Solid IR measurement, and the resultant was dried under vacuum, yielding 690 mg of beads in which the hydroxyl groups at the 6-positions were crosslinked with 4,4'-DBDI. The obtained beads were thoroughly washed with THF and the beads insoluble in THF were classified according to the particle size. Then, a column packed with 100 kg/cm$^2$ of the beads is referred to as Column IK-14 (FIG. 2).

(6) Preparation of Crosslinked Beads using 4,4-DBDI (for Column IK-15), Crosslinking using 4,4'-DBDI in an Amount of Twice as the Amount of the Item (5) of Example 3

First, 7 ml of toluene was added to 595 mg (1.44 mmol) of dried OD(6-OH)-100 beads under a nitrogen atmosphere, and the mixture was heated at 80° C. for 3 hours to swell the beads. Then, 174 mg (0.66 mmol) of 4,4'-DBDI was added thereto for reaction at 80° C. for 33 hours.

The presence of unreacted isocyanate was confirmed by Liquid IR measurement of a supernatant, and a small amount of beads was sampled to confirm that the beads became insoluble in tetrahydrofuran. After that, 592 mg (4.03 mmol) of 3,5-dimethylphenyl isocyanate was added for reaction at 80° C. for 24 hours. Then, 5 ml (excess amount) of tert-butanol was added for reaction at 80° C. for 6 hours, to thereby crush, with a bulky alcohol, a substance in which only one of the two isocyanates of 4,4-DBDI was reacted with a derivative.

The disappearance of isocyanate was confirmed by Liquid IR measurement of a supernatant, and the beads were collected through suction filtration. Then, the beads were washed with warmed methanol while being suctioned, to thereby remove urea generated from isocyanate and tert-butanol.

The absence of urea was confirmed by Solid IR measurement, and the resultant was dried under vacuum, yielding 697 mg of beads in which the hydroxyl groups at the 6-positions were crosslinked with 4,4'-DBDI. The obtained beads were thoroughly washed with THF and the beads insoluble in THF were classified according to the particle size. Then, a column packed with 100 kg/cm² of the beads is referred to as Column IK-15.

(7) Preparation of Crosslinked Beads (for Column IK-16)

First, 7 ml of toluene was added to 515 mg (1.25 mmol) of dried OD(6-OH)-100 beads under a nitrogen atmosphere, and the mixture was heated at 80° C. for 3 hours to swell the beads. Then, 82 mg (0.33 mmol) of 4,4'-diphenylmethane diisocyanate (MDI) was added thereto for reaction at 80° C. for 33 hours.

The presence of unreacted isocyanate was confirmed by Liquid IR measurement of a supernatant, and a small amount of beads was sampled to confirm that the beads became insoluble in tetrahydrofuran. After that, 356 mg (2.42 mmol) of 3,5-dimethylphenyl isocyanate was added for reaction for 24 hours. Then, 5 ml (excess amount) of tert-butanol was added for reaction for 6 hours, to thereby process, with a bulky alcohol, a substance in which only one of the two isocyanates of MDI was reacted with a derivative.

The disappearance of isocyanate was confirmed by Liquid IR measurement of a supernatant, and the beads were collected through suction filtration. Then, the beads were washed with warmed methanol while being suctioned, to thereby remove urea formed from isocyanate and tert-butanol.

The absence of urea was confirmed by Solid IR measurement, and the resultant was dried under vacuum, yielding 583 mg of beads in which the hydroxyl groups at the 6-positions were crosslinked with MDI. The obtained beads were thoroughly washed with THF and the beads insoluble in THF were classified according to the particle size. Then, a column packed with 100 kg/cm² of the beads is referred to as Column IK-16.

(8) Preparation of Crosslinked Beads (for Column IK-17)

First, 7 ml of toluene was added to 595 mg (1.44 mmol) of dried OD(6-OH)-100 beads under a nitrogen atmosphere, and the mixture was heated at 80° C. for 3 hours to swell the beads. Then, 77 mg (0.44 mmol) of tolylene-2,4-diisocyanate (2,4-TDI) was added thereto for reaction at 80° C. for 33 hours.

The presence of unreacted isocyanate was confirmed by Liquid IR measurement of a supernatant, and a small amount of beads was sampled to confirm that the beads became insoluble in tetrahydrofuran. After that, 393 mg (2.67 mmol) of 3,5-dimethylphenyl isocyanate was added for reaction for 24 hours. Then, 5 ml (excess amount) of tert-butanol was added for reaction for 6 hours, to thereby process, with a bulky alcohol, a substance in which only one of the two isocyanates of 2,4-TDI was reacted with a derivative.

The disappearance of isocyanate was confirmed by Liquid IR measurement of a supernatant, and the beads were collected through suction filtration. Then, the beads were washed with warmed methanol while being suctioned, to thereby remove urea generated from isocyanate and tert-butanol.

The absence of urea was confirmed by Solid IR measurement, and the resultant was dried under vacuum, yielding 633 mg of beads in which the hydroxyl groups at the 6-positions were crosslinked with 2,4-TDI. The obtained beads were thoroughly washed with THF and the beads insoluble in THF were classified according to the particle size. Then, a column packed with 100 kg/cm² of the beads is referred to as Column IK-17 (FIG. 2).

(9) Preparation of Crosslinked Beads (for Column IK-19)

First, 7 ml of toluene was added to 609 mg (1.48 mmol) of dried OD(6-OH)-100 beads under a nitrogen atmosphere, and the mixture was heated at 80° C. for 3 hours to swell the beads. Then, 68 mg (0.36 mmol) (excess amount) of m-xylylene diisocyanate (XDI) was added thereto for reaction at 80° C. for 33 hours.

The presence of unreacted isocyanate was confirmed by Liquid IR measurement of a supernatant, and a small amount of beads was sampled to confirm that the beads became insoluble in tetrahydrofuran After that, 359 mg (2.44 mmol) of 3,5-dimethylphenyl isocyanate was added for reaction for 24 hours. Then, 5 ml (excess amount) of tert-butanol was added for reaction for 6 hours, to thereby process, with a bulky alcohol, a substance in which only one of the two isocyanates of XDI was reacted with a derivative.

The disappearance of isocyanate was confirmed by Liquid IR measurement of a supernatant, and the beads were collected through suction filtration. Then, the beads were washed with warmed methanol while being suctioned, to thereby remove urea generated from isocyanate and tert-butanol.

The absence of urea was confirmed by Solid IR measurement, and the resultant was dried under vacuum, yielding 624 mg of beads in which the hydroxyl groups at the 6-positions were crosslinked with XDI. The obtained beads were thoroughly washed with THF and the beads insoluble in THF were classified according to the particle size. Then, a column packed with 100 kg/cm² of the beads is referred to as Column IK-19.

TABLE 3

| diisocyanate | | OD(6-OH) beads A mg | diisocyanate L mg/M % | 3,5-diMePh isocyanate N mg | Crosslinked beads B mg | THF soluble part C mg/D % |
|---|---|---|---|---|---|---|
| 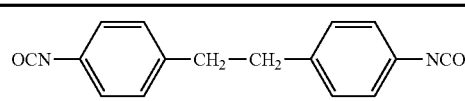 4,4'-DBDI | | 610 mg 1.48 mmol | 90 mg 0.34 mmol 46% | 646 mg 4.39 mmol | 690 mg (IK-14) | 27 mg 4% |
| 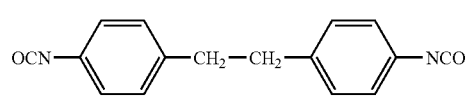 4,4'-DBDI | | 595 mg 1.44 mmol | 174 mg 0.66 mmol 92% | 592 mg 4.03 mmol | 697 mg (IK-15) | 18 mg 3% |

TABLE 3-continued

| diisocyanate | OD(6-OH) beads A mg | diisocyanate L mg/M % | 3,5-diMePh isocyanate N mg | Crosslinked beads B mg | THF soluble part C mg/D % |
|---|---|---|---|---|---|
| 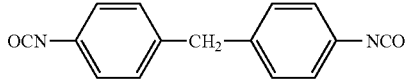 MDI | 515 mg 1.25 mmol | 82 mg 0.33 mmol 53% | 356 mg 2.42 mmol | 583 mg (IK-16) | 17 mg 3% |
| 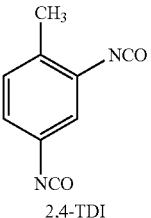 2,4-TDI | 595 mg 1.44 mmol | 77 mg 0.44 mmol 61% | 393 mg 2.67 mmol | 633 mg (IK-17) | 25 mg 4% |
| 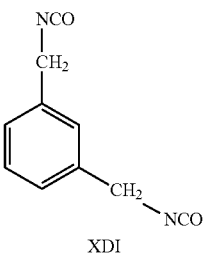 XDI | 609 mg 1.48 mmol | 68 mg 0.36 mmol 49% | 359 mg 2.44 mmol | 624 mg (IK-19) | 31 mg 5% |

The above-mentioned reactions are summarized in Table 3. Crosslinking was performed using hexamethylene diisocyanate. However, the reactivity was low, and therefore a filler being insoluble in THF could not be prepared.

(10) Optical Resolution of a Racemate by HPLC

Optical resolution of the 10 kinds of racemates (3 to 12) of Example 1 was performed using the crosslinked-beads columns (Columns IK-14 to 19) obtained by the above-mentioned operations. Hexane/2-propanol (90/10) was used as an eluent, and a flow rate was 0.2 ml/min. A theoretical plate number N was determined from a chart of benzene, and a time $t_0$ at which a substance not retained by the column passes through the column was determined from an elution time of 1,3,5-tri-tert-butylbenzene.

The evaluation results of Columns IK-14 to 17 and 19 on the optical resolution ability are shown in Tables 4 and 5. For comparison, the results of Column IK-18 which was packed with OD(6-OH)-100 beads prior to crosslinking prepared in the item (4) of Example 3 and the OD coated-type (silica gel-carried type) are also shown.

TABLE 4

| | IK-14 (100 kg/cm²) | | IK-15 (100 kg/cm²) | |
|---|---|---|---|---|
| | 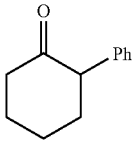 4,4'-DBDI H/I = 90/10 | | 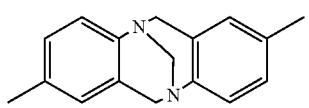 4,4'-DBDI H/I = 90/10 | |
| racemates | $k_1'$ to = 1.55 | α | $k_1'$ to = 1.49 | α |
| 2-phenylcyclohexanone | 5.81 (−) | 1.20 | 5.88 (−) | 1.20 |
| (bicyclic diamine) | 3.96 (+) | 1.40 | 4.73 (+) | 1.38 |

TABLE 4-continued
| structure | k₁' | α (col3) | k₁' (col4) | α (col5) |
|---|---|---|---|---|
| 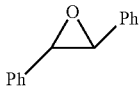 | 2.25 (+) | 1.37 | 2.70 (+) | 1.36 |
| 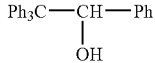 | 5.90 (+) | 1.33 | 6.96 (+) | 1.30 |
| 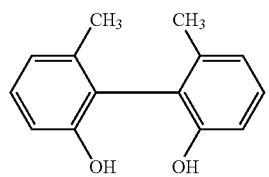 | 8.10 (−) | 2.45 | 9.51 (−) | 2.40 |
| 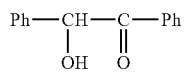 | 13.29 (+) | 1.11 | 15.49 (+) | 1.15 |
| 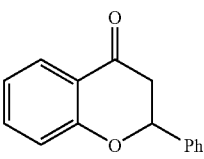 | 7.34 | 1.00 | 9.05 | 1.00 |
| Co(acac)₃ | 5.18 (+) | 1.51 | 7.24 (+) | 1.47 |
| 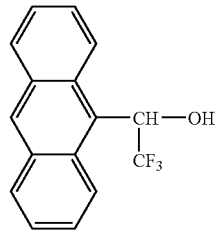 | 7.69 (−) | 1.69 | 9.15 (−) | 1.66 |
| 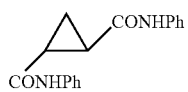 | 8.35 | 1.00 | 9.74 | 1.00 |
| | IK-16 (100 kg/cm²) |
|---|---|
| | 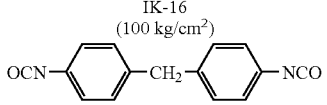 |
| | MDI |
| | H/I = 90/10 |
| racemates | k₁'    α |
| | t₀ = 1.58 |
| 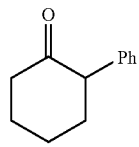 | 5.20 (−)    1.20 |

TABLE 4-continued

| Compound | Value 1 | Value 2 |
|---|---|---|
| 2,7-dimethyl-dihydroquinazoline (bridged bis-aryl diamine structure) | 3.98 (+) | 1.40 |
| trans-stilbene oxide (2,3-diphenyloxirane) | 2.23 (+) | 1.39 |
| Ph₃C—CH(OH)—Ph | 5.93 (+) | 1.34 |
| 6,6'-dimethyl-2,2'-biphenyldiol | 7.94 (−) | 2.33 |
| Ph—CH(OH)—C(=O)—Ph (benzoin) | 13.59 (+) | 1.11 |
| 2-phenyl-chroman-4-one | 7.82 | 1.00 |
| Co(acac)₃ | 5.50 (+) | 1.51 |
| 9-anthryl-(trifluoromethyl)methanol | 7.80 (−) | 1.70 |
| trans-1,2-cyclopropanedicarboxylic acid dianilide (CONHPh, CONHPh) | 8.94 | 1.00 |

Column: 25 × 0.20 cm(i.d.), flow rate: 0.2 ml/min.

TABLE 5

| | IK-17[a] (100 kg/cm²) 2,4-TDI | | IK-19[a] (100 kg/cm²) XDI | | IK-18[a] (100 kg/cm²) Non-crosslinking | | OD coated-type[b] (21 wt % on silica gel) | |
|---|---|---|---|---|---|---|---|---|
| | H/I = 90/10 | | H/I = 90/10 | | H/I = 90/10 | | H/I = 90/10 | |
| racemates | $k_1'$ to = 1.64 | α | $k_1'$ to = 1.69 | α | $k_1'$ to = 1.63 | α | $k_1'$ | α |
| 2-phenylcyclohexanone | 4.09 (−) | 1.19 | 3.40 (−) | 1.20 | 3.39 (−) | 1.09 | 0.84 (−) | 1.11 |
| Tröger's base | 3.33 (+) | 1.36 | 2.79 (+) | 1.37 | 3.33 (+) | 1.12 | 0.79 (+) | 1.21 |
| trans-stilbene oxide | 1.77 (+) | 1.37 | 1.55 (+) | 1.40 | 2.63 (+) | 1.44 | 0.54 (−) | 2.33 |
| Ph₃C—CH(OH)—Ph | 4.92 (+) | 1.28 | 4.46 (+) | 1.33 | 5.02 (+) | 1.47 | 1.02 (+) | 1.33 |
| 6,6'-dimethyl-2,2'-biphenol | 6.90 (−) | 2.47 | 6.33 (−) | 2.42 | 9.67 (−) | 2.06 | 2.04 (−) | 1.70 |
| Ph—CH(OH)—C(O)—Ph | 11.08 (+) | 1.17 | 9.26 (+) | 1.13 | 10.38 (+) | 1.14 | 2.71 (+) | 1.64 |
| flavanone | 5.84 | 1.00 | 4.94 | 1.00 | 5.31 | 1.00 | 1.03 (−) | 1.45 |
| Co(acac)₃ | 3.75 (+) | 1.41 | 2.92 (+) | 1.50 | 2.34 (+) | 1.60 | 0.29 (+) | ~1 |
| 9-anthryl-trifluoromethyl-carbinol | 6.54 (−) | 1.74 | 5.56 (−) | 1.75 | 7.23 (−) | 1.95 | 1.43 (−) | 3.28 |

TABLE 5-continued

| structure | | | | | | | | |
|---|---|---|---|---|---|---|---|---|
| (cyclopropane with two CONHPh groups) | 7.85 | 1.00 | 5.68 (−) | 1.11 | 6.48 (−) | 1.19 | 0.52 (+) | 3.21 |

[a]Column: 25 × 0.20 cm(i.d.), flow rate: 0.2 ml/min.
[b]Column: 25 × 0.20 cm(i.d.), flow rate: 0.1 ml/min.

First, the optical resolution abilities of IK-14 and IK-15 which were prepared with variations in a proportion of a crosslinking agent to be reacted, are compared. In order to investigate a change in the optical resolution ability due to the difference in a degree of crosslinking and a change in the durability against a solvent, IK-14 (equivalent to 46% of the 6-positions) and IK-15 (equivalent to 92% of the 6-positions) were prepared. However, also in the crosslinking reaction of IK-14, not all diisocyanates reacted and diisocyanate remained 33 hours after the reaction was stopped. Thus, there is presumably almost no difference in the degree of crosslinking between the IK-14 and IK-15 fillers. Therefore, changes in the optical resolution ability and durability against a solvent were hardly found. In view of the above, in order to investigate the influence on the degree of crosslinking, the amount of diisocyanate to be added must be further reduced.

Next, the optical resolution abilities of IK-14, IK-16, IK-17, and IK-19 which were prepared with different kinds of crosslinking agents, respectively, are compared. As is clear from Tables 4 and 5, there was no large difference in the optical resolution ability, and there was almost no change in the durability against a solvent. Considering the above, the kind of crosslinking agent used for preparing a crosslinking beads filler is presumably not so important.

Moreover, the elution order of trans-stilbene oxide of Columns IK-14, IK-16, IK-17, and IK-19 was reversed to that of the OD coated-type. In order to investigate whether the reversal of the order results from a change in the higher order structure caused by crosslinking, Column IK-18, which was packed with the OD(6-OH)-100 beads prior to crosslinking prepared in the item (4) of Example 3, was prepared for evaluation of optical resolution ability. It was found that the elution order of trans-stilbene oxide was reversed also in IK-18 to the order of OD coated-type. In view of the above, it is considered that the reversal of the order did not result from the crosslinking, but resulted from incomplete derivatization of the cellulose.

In order to investigate whether not only the surfaces of the beads but the polysaccharide derivatives inside the beads are effective for optical resolution, an unpacked rest of the polysaccharide derivative beads (non-crosslinking) used for IK-18 was dissolved in THF, and made to be carried on silica gel, to thereby prepare IK-22. After the evaluation of the optical resolution abilities of IK-18 and IK-22, the fillers in the columns were taken out. Then, the weights of the fillers were measured and were compared with $k_1'$. The weight of the silica gel-carried type filler was calculated by thermogravimetric analysis. The results are shown in Table 6.

TABLE 6

| racemates | IK-18[a] 300 mg Bead type H/I = 90/10 | | IK-22[b] 50 mg Silica gel-carried type H/I = 90/10 | | Amount of polysaccharide in column |
|---|---|---|---|---|---|
| | $k_1'$ | α | $k_1'$ | α | |
| 2-phenylcyclohexanone | 3.39 (−) | 1.09 | 0.47 (−) | ~1 | |
| dimethyl-dihydro-diazine compound | 3.33 (+) | 1.12 | 0.47 (+) | ~1 | |
| trans-stilbene oxide | 2.63 (+) | 1.44 | 0.22 (+) | 1.37 | |
| $Ph_3C-CH(OH)-Ph$ | 5.02 (+) | 1.47 | 0.64 (+) | 1.40 | |

TABLE 6-continued

| Structure | | | | |
|---|---|---|---|---|
| 2,2'-dihydroxy-6,6'-dimethylbiphenyl | 9.67 (−) | 2.06 | 2.15 (−) | 1.51 |
| Ph—CH(OH)—C(O)—Ph | 10.38 (+) | 1.14 | 1.42 (+) | 1.16 |
| 2-phenyl-chroman-4-one | 5.31 | 1.00 | 0.65 (−) | ~1 |
| Co(acac)$_3$ | 2.34 (+) | 1.60 | 0.31 (+) | 1.66 |
| 9-(1-trifluoroethyl)anthracene | 7.23 (−) | 1.95 | 1.01 (−) | 1.83 |
| cyclopropane-1,2-bis(CONHPh) | 6.48 (−) | 1.19 | 0.85 (−) | 1.17 |
| | 55.78 | | 8.19 | ← Total of k1' |

Column: 25 × 0.20 cm(i.d.),
flow rate $^{a)}$: 0.2 ml/min. $^{b)}$0.3 ml/min.

Comparison between the beads type (IK-18) and the silica gel-carried type (IK-22) on the amount of the polysaccharide derivative in the columns shows that the amount of the beads type is about 6 times as many as that of the silica gel-carried type (300/50). In contrast, a retention volume ($k_1'$) of the beads type is about 6.81 times as many as that of the silica gel-carried type (55.78/8.19). It is considered that, since this value is a relatively close value, the polysaccharide derivatives in the beads are effective for optical resolution. Moreover, the retention volume is not accurately proportional to the amount of polysaccharide derivatives, and a proportion of the retention volume is slightly higher. This is presumably because not only asymmetric spaces formed of polysaccharide derivative monomers interact enantioselectively, but also asymmetric spaces formed of a plurality of molecules are effective for optical resolution in the beads type filler.

Example 4

(1) Synthesis of Cellulose 3,5-dimethylphenyl carbamate OD(ran-OH) which Nonspecifically has a Hydroxyl Group in Part First, 22.5 ml of dehydrated N,N-dimethylacetamide was added to 1.5 g (9.3 mmol) of dried cellulose, and the mixture was swelled at 90° C. for 12 hours under a nitrogen atmosphere. The resultant was allowed to cool to room temperature. Then, 1.61 g of lithium chloride was added thereto, and the mixture was stirred for 28 hours at room temperature to thereby uniformly dissolve cellulose. Then, 22.5 ml of pyridine and 4.50 g (30.6 mmol) of 3,5-dimethylphenyl isocyanate were added thereto for reaction at 90° C. for 36 hours. Then, the reaction solution was dropped into methanol to collect an insoluble substance, yielding 4.17g of cellulose 3,5-dimethylphenyl carbamate OD(ran-OH).

(2) Preparation of OD(ran-OH) Beads

First, 0.375 g of OD(ran-OH) was dissolved in 45 ml of a mixed solvent of tetrahydrofuran/heptanol (2/1, v/v). The resultant mixture was dropped in 500 ml of a 0.2% aqueous sodium lauryl sulfate solution heated to 75° C. in a water bath while being stirred with a disperser at a shaft rotation number of 1,100 rpm. Also after the dropping, a surfactant solution was heated to 75° C. for distilling tetrahydrofuran off. The formed beads were collected through suction filtration, washed with methanol and dried under vacuum. OD(ran-OH) beads were obtained by repeating this process. A six blade-type shaft was used for the disperser, and a 1-L beaker was used as the vessel.

(3) Crosslinking of OD(ran-OH) Beads using Diisocyanate

First, 8 ml of toluene was added to 780 mg of dried OD(ran-OH) beads under a nitrogen atmosphere, and the mixture was heated at 85° C. for 10 hours to swell the beads. Then, 55 mg (0.22 mmol) of 4,4'-diphenylmethane diisocyanate was added thereto for reaction at 85° C. for 34 hours. A small amount of beads was sampled to confirm that the beads became insoluble in tetrahydrofuran. After that, 10 ml (excess amount) of tert-butanol was added for reaction for 5 hours. The disappearance of isocyanate was confirmed by Liquid IR measurement of a supernatant.

Then, the beads were collected through suction filtration, and were washed with warmed methanol while being suctioned, to thereby remove urea generated from isocyanate and tert-butanol. The absence of urea was confirmed by Solid IR measurement, to thereby obtain 768 mg of OD(ran-OH) beads. A beads column which was packed with the obtained beads by the same process as in the item (4) of Example 1 is referred to as Column IK-8.

(4) Optical Resolution of a Racemate by HPLC

Optical resolution of the 10 kinds of racemates (3 to 12) of Example 1 was performed using the crosslinked-beads column (Column IK-8) obtained by the above-mentioned operation. Hexane/2-propanol (90/10) was used as an eluent, and a flow rate was 0.1 ml/min. A theoretical plate number N was determined from a chart of benzene, and a time $t_0$ at which a substance not retained by the column passes through the column was determined from an elution time of 1,3,5-tri-tert-butylbenzene.

The evaluation results of the optical resolution ability of Column IK-8 are shown in Table 7. For comparison, the results of crosslinking IK-11 specifically at the 6-position and OD coated-type (silica gel-carried type) are also shown.

TABLE 7

| | IK-11 H/I = 90/10 | | IK-8 H/I = 90/10 | | OD coated-type H/I = 90/10 | |
|---|---|---|---|---|---|---|
| racemates | $k_1'$ | α | $k_1'$ | α | $k_1'$ | α |
| 2-phenylcyclohexanone | 4.63 (−) | 1.16 | 2.89 (−) | 1.18 | 0.84 (−) | 1.11 |
| Tröger's base | 3.27 (+) | 1.25 | 3.12 (+) | 1.09 | 0.79 (+) | 1.21 |
| stilbene oxide | 2.51 (−) | 1.70 | 1.76 (−) | 1.68 | 0.54 (−) | 2.33 |
| Ph₃C—CH(OH)—Ph | 5.21 (+) | 1.09 | 4.06 (+) | 1.06 | 1.02 (+) | 1.33 |
| 6,6'-dimethyl-2,2'-biphenol | 5.44 (−) | 2.27 | 4.76 (−) | 2.16 | 2.04 (−) | 1.70 |
| Ph—CH(OH)—C(=O)—Ph | 7.89 (+) | 1.36 | — | | 2.71 (+) | 1.64 |
| 2-phenyl-4-chromanone | 4.63 (−) | 1.24 | 3.65 (−) | 1.20 | 1.03 (−) | 1.45 |
| Co(acac)₃ | 1.84 (+) | 1.20 | 1.60 (+) | 1.25 | 0.29 (+) | ~1 |

TABLE 7-continued

| racemates | IK-11 H/I = 90/10 $k_1'$ | α | IK-8 H/I = 90/10 $k_1'$ | α | OD coated-type H/I = 90/10 $k_1'$ | α |
|---|---|---|---|---|---|---|
| anthracenyl-CH(OH)-CF$_3$ | 7.83 (−) | 2.41 | — | | 1.43 (−) | 3.28 |
| cyclopropane-CONHPh, CONHPh | 3.84 (+) | 1.53 | 3.76 (+) | 1.37 | 0.52 (+) | 3.21 |

Column: 25 × 0.20 cm(i.d.), flow rate: 0.1 ml/min

Since the grade of derivatization is not strictly the same between IK-11 and IK-8, they cannot be simply compared. However, as is clear from Table 7, there is a tendency that the optical resolution ability of IK-11 is overall higher than that of IK-8, and that a substance in which crosslinking is specifically performed at the 6-position can achieve a higher optical resolution ability. In macromolecule asymmetric recognition materials such as a polysaccharide derivative, the regular higher-order structure plays an important role. Thus, a higher optical resolution ability was presumably obtained by performing crosslinking specifically at the 6-position without breaking down the regular structure.

Example 5

(1) Synthesis of Cellulose 3,5-dimethylphenyl carbamate OD(6-OH)-50 having a Hydroxyl Group in Part at the 6-positions First, 150 ml of dehydrated N,N-dimethylacetamide was added to 10.15 g (62.7 mmol) of dried cellulose, and the mixture was swelled at 85° C. for 22 hours under a nitrogen atmosphere. The resultant was allowed to cool to room temperature. Then, 15.7 g of lithium chloride was added thereto, and the mixture was stirred for 0.5 hours at room temperature to thereby uniformly dissolve cellulose. Then, 155 ml of pyridine and 30.2 g (108 mmol) of triphenylmethyl chloride were added thereto for reaction at 85° C. for 31 hours. Then, 29.6 g (201 mmol) of 3,5-dimethylphenyl isocyanate was added for further reaction at 80° C. for 41 hours.

The reaction solution was sampled for measurement of infrared absorption spectrometry to confirm the presence of unreacted isocyanate in the solution. Then, the reaction solution was dropped into methanol to collect an insoluble substance, yielding cellulose 2,3-bis(3,5-dimethylphenyl-carbamoyl)-6-0-trityl cellulose.

Next, this derivative was stirred in 500 ml of 1% HCl/methanol for 42 hours for deprotection, thereby returning the groups at the 6th positions to hydroxyl groups. Thus, 24.4 g of target cellulose 2,3-bis(3,5-dimethylphenyl carbamate) was obtained.

Next, 10.4 g (22.8 mmol) of the obtained derivative was dissolved in 70 ml of pyridine, and 1.88 g (12.7 mmol) of 3,5-dimethylphenyl isocyanate was added thereto under a nitrogen atmosphere for reaction at 85° C. for 18 hours. The reaction solution was dropped into methanol to collect as an insoluble substance. The insoluble substance was dried under vacuum, yielding 9.5 g of cellulose 3,5-dimethylphenyl carbamate having a hydroxyl group(s) in part at the 6-positions. However, because the trityl group serving as a protecting group was not completely removed, the resultant was stirred in 500 ml of 1% HCl/methanol for 52 hours for further deprotection.

The resultant was washed with methanol and dried under vacuum. Then, NMR analysis showed that about 50% of the hydroxyl groups at the 6-positions of glucose rings remained. Hereinafter, this derivative is referred to as OD(6-OH)-50.

(2) Preparation of OD(6-OH)-50 Beads having Pores

Unlike the previous preparation process, an additive was added for preparing beads. More specifically, a polysaccharide derivative and an additive were dissolved in a THF/heptanol mixed solvent, and then beads were prepared in almost the same manner as before. The obtained additive-containing beads were washed with a solvent capable of dissolving only the additive, to thereby prepare beads with pores. Cellulose derivative beads with pores were produced by adding a polymer such as PNIPAM and PMMA as an additive.

25 mg of OD(6-OH)-50 and 3 mg of PNIPAM were dissolved in 3 ml of a mixed solvent of tetrahydrofuran/heptanol (2/1, v/v). The solution was dropped into 500 ml of a 0.2% aqueous solution of sodium lauryl sulfate heated to 75° C. in a water bath while being stirred with a disperser at a shaft rotation number of 1,100 rpm. After the dropping, the temperature of a surfactant solution was heated at 75° C. to distill tetrahydrofuran off. By repeating this operation, OD(6-OH)-50 beads were obtained.

The formed beads were collected through suction filtration, and were thoroughly washed with distilled water to thereby wash away only the additive. After the washing, the resultant was dried under vacuum. The obtained beads were subjected to observation with SEM, which showed that pores were formed on the surfaces of the beads. A 6 blade-type shaft was used for a shaft of the disperser, and a 200-ml beaker was used as the vessel.

(3) Crosslinking of Porous OD(6-OH)-50 Beads using Diisocyanate

First, 8 ml of toluene was added to 730 mg of dried OD(6-OH)-50 beads under a nitrogen atmosphere, and the mixture was heated at 85° C. for 21 hours to swell the beads. Then, 43 mg (0.17 mmol) of 4,4'-diphenylmethane diisocyanate was added thereto for reaction at 85° C. 24 hours. A small amount of beads was sampled to confirm that the beads became insoluble in tetrahydrofuran. After that, 220 mg (1.5 mmol) of 3,5-dimethylphenyl isocyanate was added for reaction for 24 hours. Then, 10 ml (excess amount) of tert-butanol was added for reaction for 2 hours. The disappearance of isocyanate was confirmed by Liquid IR measurement of a supernatant, and the beads were collected through suction filtration. Then, the beads were washed with warmed methanol while being suctioned, to thereby remove urea generated from isocyanate and tert-butanol.

The absence of urea was confirmed by Solid IR measurement, to thereby obtain 720 mg of OD(6-OH)-50 beads. A beads column which was packed with the obtained beads in the same procedure as in 3-1-4 is referred to as Column IK-4 (FIG. 1).

(4) Optical Resolution of a Racemate by HPLC

Optical resolution of the 10 kinds of racemates (3 to 12) of Example 1 was performed using the crosslinked-beads column (Column IK-4) obtained by the above-mentioned operation. Hexane/2-propanol (90/10) was used as an eluent, and a flow rate was 0.1 ml/min. A theoretical plate number N was determined from a chart of benzene, and a time $t_0$ at which a substance not retained by the column passes through the column was determined from an elution time of 1,3,5-tri-tert-butylbenzene.

The evaluation results of the optical resolution ability of Column IK-4 (FIG. 1) are shown in Table 8. For comparison, the results of Column IK-2 (FIG. 1) with no pore and an OD coated-type (silica gel-carried type) are also shown.

TABLE 8

| | racemates | Column IK-2[a] additive: none $k_1'$ | α | Column IK-4[b] additive: PNIPAM $k_1'$ | α | coated-type[a] $k_1'$ | α |
|---|---|---|---|---|---|---|---|
| 1 | 2-phenylcyclohexanone | 3.28 (−) | 1.21 | 4.42 (−) | 1.25 | 0.84 (−) | 1.11 |
| 2 | Tröger's base | 3.27 (+) | 1.12 | 3.29 (+) | 1.26 | 0.79 (+) | 1.21 |
| 3 | trans-stilbene oxide | 1.99 (−) | 1.81 | 2.29 (−) | 1.50 | 0.54 (−) | 2.33 |
| 4 | Tr—CH(OH)—Ph | 4.20 (+) | 1.20 | 4.96 (+) | 1.21 | 1.02 (+) | 1.33 |
| 5 | 1,1'-bi-2-naphthol derivative | 4.68 (−) | 2.87 | 7.28 (−) | 3.21 | 2.04 (−) | 1.70 |
| 6 | Ph—C(O)—CH(OH)—Ph | 7.28 (+) | 1.37 | 8.59 (+) | 1.28 | 2.71 (+) | 1.64 |
| 7 | flavanone | 4.18 (−) | 1.26 | 4.84 (−) | 1.23 | 1.03 (−) | 1.45 |
| 8 | Co(acac)$_3$ | 1.77 (+) | 1.31 | 2.18 (+) | 1.28 | 0.29 (+) | ~1 |
| 9 | F$_3$C—CH(OH)—(9-anthryl) | 8.26 (−) | 2.94 | 10.57 (−) | 2.43 | 1.43 (−) | 3.28 |

TABLE 8-continued

| | | Column IK-2[a] additive: none | | Column IK-4[b] additive: PNIPAM | | coated-type[a] | |
|---|---|---|---|---|---|---|---|
| | racemates | $k_1'$ | α | $k_1'$ | α | $k_1'$ | α |
| 10 |  | 3.38 (+) | 1.73 | 4.47 (+) | 1.40 | 0.52 (+) | 3.21 |

Eluent, hexane - 2-propanol (90:10).
[a]Column: 25 × 0.20 cm (i.d.), flow rate: 0.1 ml/min.
[b]Column: 25 × 0.20 cm (i.d.), flow rate: 0.15 ml/min.

In order to increase the proportion of a polysaccharide derivative capable of participating in optical resolution in a column, preparation of porous cellulose beads with a large surface area was attempted. However, it was found from the experiment of Example that not only the bead surfaces but the polysaccharide derivatives in the beads are efficiently effective for optical resolution in the polysaccharide derivative beads filler. Later, it was found that the fractionation ability is not improved even if the surface area is enlarged.

Example 6

(1) Synthesis of Cellulose 3,5-dimethylphenyl carbamate OD(6-Tr) having Trityl Groups at the 6-positions First, 15 ml of dehydrated N,N-dimethylacetamide was added to 1.0 g (6.2 mmol) of dried cellulose, and the mixture was swelled under a nitrogen atmosphere at 80° C. for 4 hours. The resultant was allowed to cool to room temperature. Then, 0.95 g of LiCl was added thereto, and the mixture was stirred for 1 hour at room temperature. The cellulose was not completely dissolved, and no uniform solution was obtained.

Then, 15 ml of pyridine and 2.15 g (7.71 mmol) of triphenyl methyl chloride were added thereto for reaction at 85° C. for 60 hours, but the reaction solution was not uniform. Thus, the reaction solution was collected once. For performing tritylation again, the reaction solution was dropped into methanol to collect as an insoluble part. The insoluble part was dried under vacuum. To 1.80 g of the obtained derivative, 15 ml of dehydrated N,N-dimethylacetamide was added, and the mixture was swelled at 80° C. for 5 hours under a nitrogen atmosphere. The resultant was allowed to cool to room temperature. Then, 1.49 g of LiCl was added thereto, and the mixture was stirred for 1 hour at room temperature to thereby uniformly dissolve the cellulose derivative. Then, 15 ml of pyridine and 0.70 g (2.50 mmol) of triphenyl methyl chloride were added thereto for reaction at 80° C. for 20 hours.

Then, 2.33 g (15.9 mmol) of 3,5-dimethylphenyl isocyanate was added thereto for reaction at 80° C. for 24 hours. The reaction solution was sampled for measurement of infrared absorption spectrometry to confirm the presence of unreacted isocyanate in the solution. Then, the reaction solution was dropped into methanol to collect an insoluble substance, yielding 3.47 g of cellulose 2,3-bis(3,5-dimethylphenylcarbamoyl)-6-0-trityl cellulose OD(6-Tr)-040618.

(2) Preparation of OD(6-Tr) Beads

First, 0.25 g of OD(6-Tr)-040618 was dissolved in 15 ml of a mixed solvent of tetrahydrofuran/heptanol (2/1, v/v). The resultant mixture was dropped in 500 ml of a 0.2% aqueous sodium lauryl sulfate solution heated to 75° C. in a water bath while being stirred with a disperser at a shaft rotation number of 1,100 rpm. Also after the dropping, a surfactant solution was heated to 75° C. for distilling tetrahydrofuran off. The formed beads were collected through suction filtration and washed with methanol.

After washing, the beads were dried under vacuum and classified with a 20-μm filter, yielding 0.14 g of OD(6-Tr)-040618 beads whose particle sizes range from 3 to 10. In the process, the yield of the beads was about 55%. The beads were repeatedly subjected to this operations eight times. A six blade-type shaft was used for the disperser, and a 1-L beaker was used as the vessel. The obtained beads were subjected to observation with a SEM.

(3) Preparation of OD(6-OH) Beads

First, 1.09 g of OD(6-Tr)-040618 beads prepared in the above item (2) was stirred in 100 ml of 2% HCl/methanol at room temperature for 36 hours for deprotection, thereby returning the groups at the 6-positions to hydroxyl groups. The resultant was washed with methanol and dried under vacuum, yielding 0.81 g of target OD(6-OH) beads. NMR and elementary analysis confirmed that 99% or more of the trityl groups introduced into the 6-positions were removed.

(4) Crosslinking of OD(6-OH) Beads using Diisocyanate

First, 6 ml of toluene was added to 526 mg of the dried OD(6-OH) beads prepared in (3) of Example 6, under a nitrogen atmosphere, and the mixture was heated at 85° C. for 15 hours to swell the beads. Then, 37 mg (0.15 mmol) of 4,4'-diphenylmethane diisocyanate was added thereto for reaction at 85° C. for 37 hours. A small amount of beads was sampled to confirm that the beads became insoluble in tetrahydrofuran. After that, 550 mg (3.7 mmol) of 3,5-dimethylphenyl isocyanate was added for reaction for 42 hours. Then, 10 ml (excess amount) of tert-butanol was added for reaction for 4 hours. The disappearance of isocyanate was confirmed by Liquid IR measurement of a supernatant, and the beads were collected through suction filtration. Then, the beads were washed with warmed methanol while being suctioned, to thereby remove urea formed from isocyanate and tert-butanol.

The absence of urea was confirmed by Solid IR measurement, to thereby obtain 530 mg of OD(6-OH) beads. A beads column which was packed with the obtained beads in the same procedure as in the item (4) of Example 1 is referred to as Column IK-5-2 (FIG. 1).

(5) Optical Resolution of a Racemate by HPLC

Optical resolution of the 10 kinds of racemates (3 to 12) of Example 1 was performed using the crosslinked-beads column (Column IK-5-2) obtained by the above-mentioned operation. Hexane/2-propanol (90/10) was used as an eluent, and a flow rate was 0.1 ml/min. A theoretical plate number N was determined from a chart of benzene, and a time $t_0$ at which a substance not retained by the column passes through the column was determined from an elution time of 1,3,5-tri-tert-butylbenzene.

After the preparation of the beads, even if the trityl groups as protecting groups at the 6-positions were removed, the surface area calculated by BET hardly changed. Therefore, it was found that porous polysaccharide derivative beads could not be prepared according to this process (surface area of the beads before deprotection: 2.8 $m^2/g$ and the surface area of the beads after deprotection: 3.0 $m^2/g$).

The evaluation results of the optical resolution ability of Column IK-5-2 are shown in Table 9. For comparison, the results of OD coated-type (silica gel-carried type) are also shown.

TABLE 9

| racemates | IK-11 H/I = 90/10 $k_1'$ | IK-11 H/I = 90/10 α | IK-5-2 H/I = 90/10 $k_1'$ | IK-5-2 H/I = 90/10 α | OD coated-type[b] H/I = 90/10 $k_1'$ | OD coated-type[b] H/I = 90/10 α |
|---|---|---|---|---|---|---|
| 2-phenylcyclohexanone | 4.63 (−) | 1.16 | 4.00 (−) | 1.19 | 0.84 (−) | 1.11 |
| 2,8-dimethyl-6H,12H-5,11-methanodibenzo[b,f][1,5]diazocine | 3.27 (+) | 1.25 | 3.32 (+) | 1.25 | 0.79 (+) | 1.21 |
| trans-stilbene oxide (2,3-diphenyloxirane) | 2.51 (−) | 1.70 | 2.60 (−) | 1.25 | 0.54 (−) | 2.33 |
| $Ph_3C$—CH(OH)—Ph | 5.21 (+) | 1.09 | 5.06 (+) | 1.22 | 1.02 (+) | 1.33 |
| 6,6'-dimethyl-2,2'-biphenol | 5.44 (−) | 2.27 | 6.47 (−) | 2.08 | 2.04 (−) | 1.70 |
| Ph—CH(OH)—C(=O)—Ph (benzoin) | 7.89 (+) | 1.36 | 9.60 (+) | 1.24 | 2.71 (+) | 1.64 |
| 2-phenyl-4-chromanone | 4.63 (−) | 1.24 | 5.33 (−) | 1.38 | 1.03 (−) | 1.45 |
| Co(acac)$_3$ | 1.84 (+) | 1.20 | 2.81 (+) | 1.38 | 0.29 (+) | ~1 |
| 9-anthryl-2,2,2-trifluoroethanol | 7.83 (−) | 2.41 | 7.22 (−) | 2.15 | 1.43 (−) | 3.28 |
| trans-1,2-bis(N-phenylcarbamoyl)cyclopropane | 3.84 (+) | 1.53 | 7.36 (+) | ~1 | 0.52 (+) | 3.21 |

[a] Column: 25 × 0.20 cm(i.d.), flow rate: 0.1 ml/min

As in Example 5, in order to increase the proportion of a polysaccharide derivative capable of participating in optical resolution in a column, preparation of porous cellulose derivative beads with a large surface area was attempted. However, it was found from the experiment of Example 3 that not only the bead surfaces but the polysaccharide derivatives in the beads are efficiently effective for optical resolution in the polysaccharide derivative beads filler. Later, it was found that the fractionation ability is not improved even if the surface area is enlarged.

Example 7

Large-Scale Separation of 2,2,2-trifluoro-1-(9-anthryl)ethanol

Figure 3:
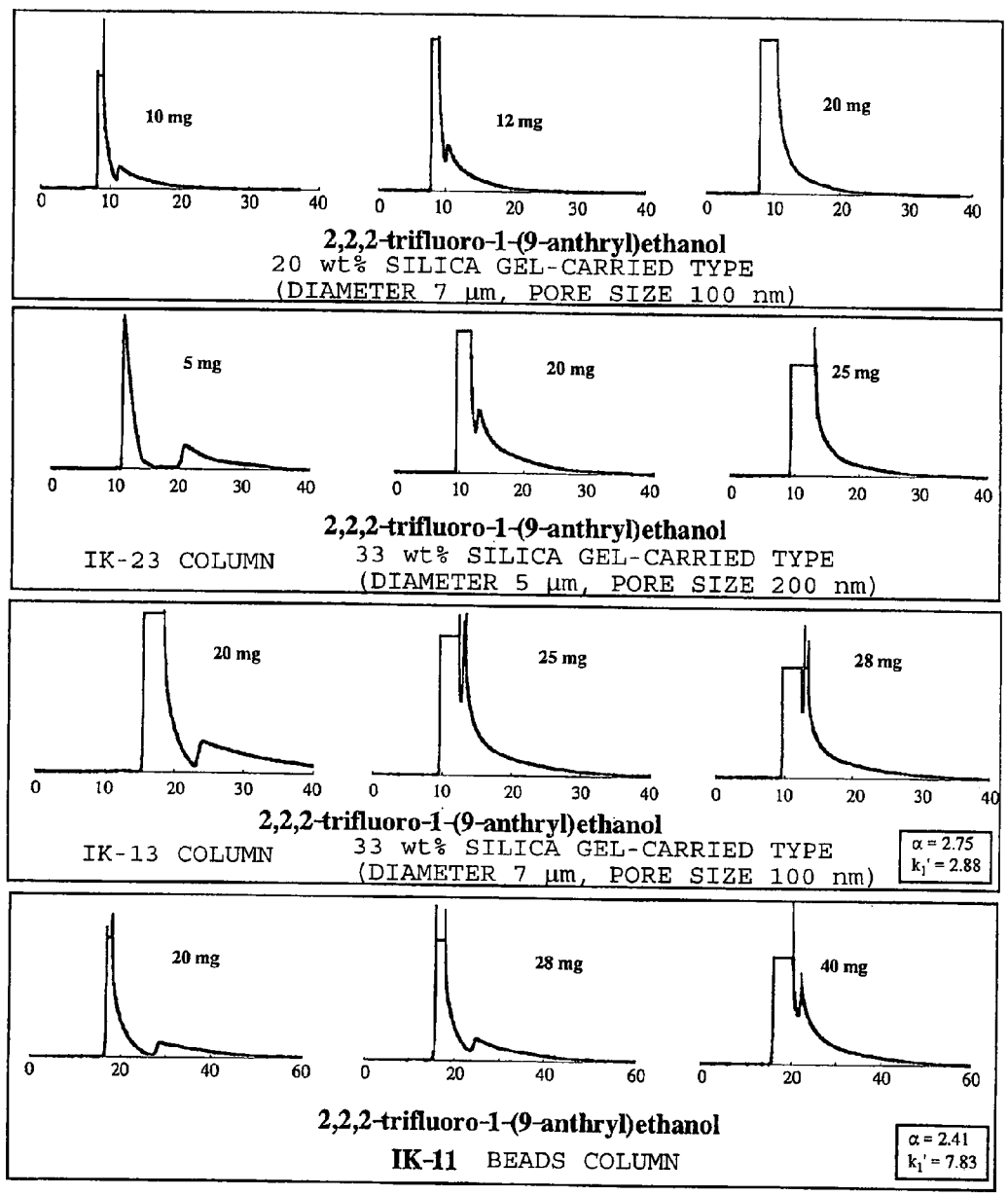
FIG. 3 shows HPLC charts of Example 7.

A column packed with beads contains a larger amount of polysaccharide derivative compared with a conventional silica gel carried-type column of the same size. Thus, it is expected that the column packed with beads can separate a larger amount of racemate at one time than the conventional silica gel carried-type column. The amount of racemate 2,2,2-trifluoro-1-(9-anthryl)ethanol that can be separated at one time was examined by using the Column IK-11 prepared in Example 2 and the silica gel carried-type column (FIG. 3).

In this case, the racemate was dissolved in a solvent whose composition is the same as that of the eluent to prepare 57 mg of solution, and optical resolution was performed using the solution. The amount of the racemate providing overlapping peaks of two enantiomers in the obtained chart was referred to as the maximum amount of the compound that can be separated by the column. The following three silica gel-carried type columns were used.

20 wt % (TG result) silica gel-carried type (diameter of 7 μm, pore size of 100 nm)

33 wt % (TG result) silica gel-carried type (diameter of 5 μm, pore size of 200 nm)

33 wt % (TG result) silica gel-carried type (diameter of 7 μm, pore size of 100 nm)

Of the silica gel-carried type columns, the 20 wt % silica gel-carried type column whose carried amount was the smallest could not separate 20 mg of racemates, and was the least suitable for fractionation. Further, the reason why the fractionation ability was different between the two kinds of 33 wt % silica gel-carried type columns in which the silica gel size and the pore size were different from each other, was presumably that the amounts of filler in the columns were different from each other. Thus, it had been expected that a large amount of polysaccharide derivative might be retained on silica gel having a smaller size and large sized pores, and that the carried amount was increased. However, the carried amount was not increased by changing the size of silica gel and the pore size.

Next, the silica gel-carried type column and the beads type column of the same size are compared for the fractionation ability. With respect to the 33 wt % (TG result) silica gel-carried type column (diameter of 7 μm, pore size of 100 nm) which was able to separate best among the silica gel-carried type columns above, when 28 mg of racemate was injected at once, two peaks were almost overlapped. With respect to the beads type column, even if 28 mg of racemates were injected at once, two clearly separated peaks were observed, and also when 40 mg of racemates were injected at once, two separated peaks were observed.

As is clear from the above, it was found that the beads type column has higher fractionation ability than the silica gel-carried type column (33 wt %) that was prepared in such a manner that the carried amount was increased as much as possible.

Example 8

(1) Synthesis of Amylose 3,5-dimethylphenyl carbamate AD(6-OH)-20 having Hydroxyl Groups in Part at the 6-positions First, 22.5 ml of dehydrated N,N-dimethylacetamide was added to 1.5 g (9.3 mmol) of dried amylose, and the mixture was swelled at 85° C. for 5 hours under a nitrogen atmosphere. The resultant was allowed to cool to room temperature. Then, 1.55 g of lithiumchloride was added thereto, and the mixture was stirred for 0.5 hour at room temperature to thereby uniformly dissolve amylose. Then, 22.5 ml of pyridine and 3.35 g (12.0 mmol) of triphenylmethyl chloride were added thereto for reaction at 85° C. for 43 hours. Then, 3.35 g (22.8 mmol) of 3,5-dimethylphenyl isocyanate was added for further reaction at 85° C. for 27 hours.

The reaction solution was sampled for measurement of infrared absorption spectrometry to confirm the presence of unreacted isocyanate in the solution. Then, the reaction solution was dropped into methanol to collect as an insoluble substance, yielding amylose 2,3-bis(3,5-dimethylphenylcarbamoyl)-6-O-tritylcellulose.

Next, this derivative was stirred in 300 ml of 1% HCl/methanol for 38 hours at room temperature for deprotection, thereby returning the groups at the 6-positions to hydroxyl groups. The resultant was washed with methanol and dried under vacuum, yielding 3.98 g of target amylose 2,3-bis(3,5-dimethylphenyl carbamate).

Next, 3.9 g of the obtained derivative was dissolved in 20 ml of pyridine, and 0.59 g (4.0 mmol) of 3,5-dimethylphenylisocyanate was added thereto under a nitrogen atmosphere for reaction at 85° C. for 20 hours. The reaction solution was dropped into methanol to collect as an insoluble substance. The insoluble substance was dried under vacuum, yielding 2.5 g of amylose 3,5-dimethylphenyl carbamate which has hydroxyl groups in part at the 6-positions. The NMR analysis showed that about 50% of the hydroxyl groups at the 6-positions of the glucose rings remained. Hereinafter, this derivative is referred to as AD(6-OH)-50.

(2) Preparation of Amylose Derivative Beads (AD(6-OH)-50 Beads))

First, 0.25 g of AD(6-OH)-50 beads was dissolved in 15 ml of a mixed solvent of tetrahydrofuran/heptanol (2/1, v/v). The resultant mixture was dropped in 500 ml of a 0.2% aqueous sodium lauryl sulfate solution heated to 75° C. in a water bath while being stirred with a disperser at a shaft rotation number of 1,100 rpm. Also after the dropping, a surfactant solution was heated to 75° C. for distilling tetrahydrofuran off.

The formed beads were collected through suction filtration and washed with methanol. After washing, beads classified with a 20-μm filter were dried under vacuum, yielding 0.18 g of AD(6-OH)-50 beads whose particle sizes range from about 3 to 10 μm. In the process, the yield of the beads was about 72%. This operation was repeated, yielding 0.71 g of AD(6-OH)-50 beads. A six blade-type shaft was used for the disperser, and a 1 L beaker was used as the vessel.

(3) Crosslinking of an Amylose Derivative Bead using Diisocyanate

First, 8 ml of toluene was added to 0.71 g of dried AD(6-OH)-50 beads under a nitrogen atmosphere, and the mixture was heated at 85° C. for 10 hours to swell the beads. Then, 42 mg (0.17 mmol) of 4,4'-diphenylmethane diisocyanate was added thereto for reaction at 85° C. for 27 hours. Then, 290 mg (2.0 mmol) of 3,5-dimethylphenyl isocyanate was added for reaction at 85° C. for 22 hours. The presence of unreacted isocyanate was confirmed by Liquid IR measurement of a supernatant, and a small amount of beads was sampled to confirm that the beads became insoluble in tetrahydrofuran.

After that, 10 ml of tert-butanol (excess amount) was added for reaction for 1 hour. Then, the disappearance of isocyanate was confirmed by Liquid IR measurement of a supernatant, and the beads were collected through suction filtration. Then, the beads were washed with warmed methanol while being suctioned, to thereby remove urea formed from isocyanate and tert-butanol.

The absence of urea was confirmed by Solid IR measurement, to thereby obtain 0.74 g of amylose derivative crosslinked beads. A beads column which was packed with the obtained beads in the same procedure as in the item (4) of Example 1 is referred to as Column IK-6 (FIG. 1).

(4) Optical Resolution of a Racemate by HPLC

Optical resolution of the 10 kinds of racemates (3 to 12) of Example 1 was performed using the crosslinked-beads column (Column IK-6) obtained by the above-mentioned operation. Hexane/2-propanol (90/10) was used as an eluent, and a flow rate was 0.1 ml/min. A theoretical plate number N was determined from a chart of benzene, and a time $t_0$ at which a substance not retained by the column passes through the column was determined from an elution time of 1,3,5-tri-tert-butylbenzene.

The evaluation results of the optical resolution ability of Column IK-6 are shown in Table 10. For comparison, the results of AD coated-type (silica gel-carried type) are also shown.

TABLE 10

| Compound | column IK-6 $k_1'$ | column IK-6 $\alpha$ | AD coated-type $k_1'$ | AD coated-type $\alpha$ |
|---|---|---|---|---|
| 2-phenylcyclohexanone | 3.17 (−) | ~1 | 0.43 (−) | ~1 |
| (dihydroquinoxaline dimer structure) | 2.80 (+) | 1.18 | 1.76 (+) | 1.76 |
| trans-stilbene oxide | 1.52 (+) | 1.43 | 0.30 (+) | 3.26 |
| Tr—CH(OH)—Ph | 4.71 (+) | 1.40 | 2.19 (+) | 2.05 |
| 6,6'-dimethyl-2,2'-biphenol | 6.44 (−) | 1.41 | 2.46 (−) | 1.81 |
| Ph—C(=O)—CH(OH)—Ph | 9.99 (+) | 1.16 | 2.39 (−) | 1.29 |
| 2-phenyl-chroman-4-one | 4.87 (+) | 1.26 | 0.69 (+) | ~1 |
| Co(acac)$_3$ | 3.65 | 1.00 | 0.19 (−) | ~1 |
| 9-(1-hydroxy-2,2,2-trifluoroethyl)anthracene | 3.97 (+) | 1.04 | 1.08 (+) | 1.24 |
| trans-1,2-bis(N-phenylcarbamoyl)cyclopropane | 9.32 (+) | 1.32 | 1.81 (+) | 2.07 |

Eluent, hexane - 2-propanol (90:10). Column: 25 × 0.20 cm(i.d.), flow rate: 0.1 ml/min.

As compared with the conventional silica gel-carried type column, because Column IK-6 has no carrier, the proportion of the polysaccharide derivatives which interact with the racemates in the column was increased, and the $k_1'$ value became markedly large. However, as compared with the carried type, the α values were lowered overall. This is presumably because a part of the regular higher-order structure of polysaccharide which plays an important role in optical resolution was collapsed by crosslinking. This result differs from the result of the cellulose derivative beads whose α values hardly changed between the beads type column and the carried type column. This presumably shows that the original structure of an amylose derivative sensitively changes owing to incomplete derivatization and crosslinking, and therefore the regular higher-order structure is more likely to be collapsed than the cellulose derivative.

Example 9

First, 22.5 ml of dehydrated N,N-dimethylacetamide was added to 1.5 g (9.3 mmol) of dried cellulose, and the mixture was swelled at 90° C. for 12 hours under a nitrogen atmosphere. The resultant was allowed to cool to room temperature. Then, 1.61 g of lithium chloride was added thereto, and the mixture was stirred for 28 hours at room temperature to thereby uniformly dissolve cellulose. Then, 22.5 ml of pyridine and 4.50 g (30.6 mmol) of 3,5-dimethylphenyl isocyanate were added thereto for reaction at 90° C. for 36 hours. The reaction solution was dropped into methanol to collect as an insoluble substance, yielding 4.17 g of cellulose 3,5-dimethylphenylcarbamate OD (ran-OH). As a result, a derivative in which about 70 to 80% of the hydroxyl groups at the 2, 3, and 6-positions of the glucose rings were randomly substituted with phenylcarbamate was obtained.

The invention claimed is:

1. A process for producing a bead for enantiomeric isomer resolution comprising a polysaccharide derivative having a structure crosslinked with a crosslinking agent at a hydroxyl group that randomly remains at any of 2-, 3- and 6- positions of constituent units of the polysaccharide and the average number of remaining hydroxyl groups in all the constituent units of the polysaccharide derivative is one or less, the method comprising the steps of:

reacting a derivative-forming compound in an amount required for converting 66 to 95% of all the hydroxyl groups contained in a polysaccharide into carbamate groups to thereby obtain a polysaccharide derivative;

adding dropwise an organic solvent solution of the polysaccharide derivative to aqueous solution of a surfactant while being stirred to thereby produce beads;

taking out the beads and, optionally, drying the beads after washing them; and reacting the beads with a crosslinking agent in the organic solvent to thereby react a hydroxyl group that randomly remains at any of the 2-, 3- and 6- positions in the constituent units of the polysaccharide with the crosslinking agent to thereby obtain a reaction mixture containing beads having a crosslinked structure.

2. The process of claim 1, wherein the organic solvent solution is a mixed solvent formed from a non-alcoholic organic solvent capable of dissolving the polysaccharide derivative and a $C_{1-22}$ alcohol, the content of the $C_{1-22}$ alcohol in the mixed solvent being 5 vol % of more.

3. The process of claim 1, wherein the polysaccharide derivative is a cellulose derivative or an amylose derivative.

4. The process of claim 1, wherein the bead has a particle size in the range of from 1 to 30 μm.

5. The process of claim 1, wherein the surfactant is an anionic surfactant.

6. The process of claim 5, wherein the anionic surfactant is sodium lauryl sulfate.

* * * * *